(12) United States Patent
Xiao et al.

(10) Patent No.: US 11,051,882 B2
(45) Date of Patent: *Jul. 6, 2021

(54) HIGH-VOLTAGE ANALOG CIRCUIT PULSER

(71) Applicant: Pulse Biosciences, Inc., Hayward, CA (US)

(72) Inventors: Shu Xiao, Norfolk, VA (US); Brian G. Athos, San Francisco, CA (US); Mark P. Kreis, San Francisco, CA (US); David J. Danitz, San Jose, CA (US); Darrin R. Uecker, San Mateo, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/693,078

(22) Filed: Nov. 22, 2019

(65) Prior Publication Data

US 2020/0085498 A1    Mar. 19, 2020

Related U.S. Application Data

(63) Continuation of application No. 15/148,344, filed on May 6, 2016, now Pat. No. 10,548,665.

(Continued)

(51) Int. Cl.
*A61B 18/12* (2006.01)
*A61B 18/18* (2006.01)
(Continued)

(52) U.S. Cl.
CPC .............. *A61B 18/18* (2013.01); *A61N 1/32* (2013.01); *A61N 1/40* (2013.01); *H03K 3/017* (2013.01);
(Continued)

(58) Field of Classification Search
CPC ........... A61B 2018/00613; A61B 2018/00773; A61B 2018/00791; A61B 2018/00827;
(Continued)

(56) References Cited

U.S. PATENT DOCUMENTS 5,568,035 A    10/1996  Kato et al.
5,635,776 A     6/1997  Imi
(Continued)

FOREIGN PATENT DOCUMENTS

EP        2160992 A2    3/2010
JP     2009-90113 A    4/2009
(Continued)

OTHER PUBLICATIONS

USPTO_OA _dated _Apr. 2005_from_AppNo._15347729—14_ pages.

(Continued)

*Primary Examiner* — Jaymi E Della
*Assistant Examiner* — Sean W Collins

(57) ABSTRACT

A sub-microsecond pulsed electric field generator is disclosed. The field generator includes a controller, which generates a power supply control signal and generates a pulse generator control signal, and a power supply, which receives the power supply control signal and generates one or more power voltages based on the received power supply control signal. The field generator also includes a pulse generator which receives the power voltages and the pulse generator control signal, and generates one or more pulses based on the power voltages and based on the pulse generator control signal. In some embodiments, the controller receives feedback signals representing a value of a characteristic of or a result of the pulses and generates at least one of the power supply control signal and the pulse generator control signal based on the received feedback signals.

25 Claims, 26 Drawing Sheets

Related U.S. Application Data

(60) Provisional application No. 62/301,477, filed on Feb. 29, 2016.

(51) Int. Cl.
*A61N 1/32* (2006.01)
*A61N 1/40* (2006.01)
*H03K 3/57* (2006.01)
*H03K 3/017* (2006.01)
*H03K 17/687* (2006.01)
*A61B 18/00* (2006.01)
*A61B 18/14* (2006.01)

(52) U.S. Cl.
CPC .............. H03K 3/57 (2013.01); H03K 17/687 (2013.01); *A61B 18/1206* (2013.01); *A61B 2018/00291* (2013.01); *A61B 2018/00577* (2013.01); *A61B 2018/00642* (2013.01); *A61B 2018/00714* (2013.01); *A61B 2018/00791* (2013.01); *A61B 2018/00827* (2013.01); *A61B 2018/00875* (2013.01); *A61B 2018/00892* (2013.01); *A61B 2018/143* (2013.01); *A61B 2018/1467* (2013.01); *A61B 2217/005* (2013.01); *A61B 2505/05* (2013.01)

(58) Field of Classification Search
CPC .......... A61B 2018/00892; A61N 1/327; H03K 3/57; H03K 7/08; H03K 17/063; H03K 17/74
USPC ............. 307/108; 323/251; 331/6; 315/5.39, 315/5.45
See application file for complete search history.

(56) References Cited

U.S. PATENT DOCUMENTS

| | | | |
|---|---|---|---|
| 5,774,348 A | 6/1998 | Druce et al. | |
| 5,902,272 A | 5/1999 | Eggers et al. | |
| 5,907,484 A | 5/1999 | Kowshik et al. | |
| 6,008,690 A | 12/1999 | Takeshima et al. | |
| 6,017,354 A | 1/2000 | Culp et al. | |
| 6,026,003 A | 2/2000 | Moore et al. | |
| 6,048,789 A | 4/2000 | Vines et al. | |
| 6,137,276 A | 10/2000 | Rudolph | |
| 6,190,381 B1 | 2/2001 | Olsen et al. | |
| 6,326,177 B1 | 12/2001 | Schoenbach et al. | |
| 6,831,377 B2 | 12/2004 | Yampolsky et al. | |
| 7,496,401 B2 | 2/2009 | Bernabei | |
| 7,767,433 B2 | 8/2010 | Kuthi et al. | |
| 7,855,904 B2 | 12/2010 | Kirbie et al. | |
| 7,937,143 B2 | 5/2011 | Demarais et al. | |
| 8,000,813 B2 | 8/2011 | Schoenbach et al. | |
| 8,512,334 B2 | 8/2013 | Nuccitelli et al. | |
| 8,688,227 B2 | 4/2014 | Nuccitelli et al. | |
| 8,822,222 B2 | 9/2014 | Beebe et al. | |
| 9,101,337 B2 | 8/2015 | Hoegerle et al. | |
| 9,101,764 B2 | 8/2015 | Nuccitelli et al. | |
| 9,168,373 B2 | 10/2015 | Nuccitelli et al. | |
| 9,724,155 B2 | 8/2017 | Nuccitelli et al. | |
| 9,918,790 B2 | 3/2018 | Zemlin et al. | |
| 10,070,914 B2 | 9/2018 | Schoenbach et al. | |
| 10,097,085 B2 | 10/2018 | Cadilhon et al. | |
| 10,252,050 B2 | 4/2019 | Kreis et al. | |
| 10,548,665 B2 * | 2/2020 | Xiao | A61N 1/32 |
| 10,874,451 B2 * | 12/2020 | Athos | H03K 3/57 |
| 2001/0025177 A1 | 9/2001 | Woloszko et al. | |
| 2002/0193833 A1 | 12/2002 | Dimmer et al. | |
| 2003/0204161 A1 | 10/2003 | Ferek-Petric | |
| 2003/0233087 A1 | 12/2003 | Chen et al. | |
| 2004/0080964 A1 | 4/2004 | Buchmann | |
| 2004/0240241 A1 | 12/2004 | Chueh et al. | |
| 2006/0062074 A1 | 3/2006 | Gundersen et al. | |
| 2006/0079886 A1 | 4/2006 | Orszulak et al. | |
| 2006/0090723 A1 | 5/2006 | Stuart | |
| 2006/0139977 A1 | 6/2006 | Oicles et al. | |
| 2007/0066957 A1 | 3/2007 | Demarais et al. | |
| 2007/0129626 A1 | 6/2007 | Mahesh et al. | |
| 2008/0077189 A1 | 3/2008 | Ostroff et al. | |
| 2008/0031337 A1 | 9/2008 | Krishnaswamy et al. | |
| 2008/0231337 A1 | 9/2008 | Krishnaswamy et al. | |
| 2009/0065444 A1 | 3/2009 | Alley | |
| 2009/0198231 A1 | 8/2009 | Esser et al. | |
| 2009/0299362 A1 | 12/2009 | Long et al. | |
| 2010/0038971 A1 | 2/2010 | Sanders et al. | |
| 2010/0042095 A1 | 2/2010 | Bigley et al. | |
| 2010/0063496 A1 | 3/2010 | Trovato et al. | |
| 2010/0240995 A1 | 9/2010 | Nuccitelli et al. | |
| 2010/0318082 A1 | 12/2010 | Nuccitelli et al. | |
| 2010/0331758 A1 | 12/2010 | Davalos et al. | |
| 2011/0015630 A1 | 1/2011 | Azure | |
| 2011/0118729 A1 | 5/2011 | Heeren et al. | |
| 2011/0144641 A1 | 6/2011 | Dimalanta et al. | |
| 2011/0160514 A1 | 6/2011 | Long et al. | |
| 2011/0270249 A1 | 11/2011 | Utley et al. | |
| 2012/0223583 A1 | 9/2012 | Cooley et al. | |
| 2012/0277763 A1 | 11/2012 | Greenblatt et al. | |
| 2012/0310230 A1 | 12/2012 | Willis et al. | |
| 2012/0315704 A1 | 12/2012 | Beebe et al. | |
| 2013/0018441 A1 | 1/2013 | Childs | |
| 2013/0041443 A1 | 2/2013 | Weissberg et al. | |
| 2013/0150935 A1 | 6/2013 | Weissberg et al. | |
| 2013/0267943 A1 * | 10/2013 | Hancock | A61B 18/1815 606/33 |
| 2013/0302409 A1 | 11/2013 | Fuchs et al. | |
| 2013/0345697 A1 | 12/2013 | Garcia et al. | |
| 2014/0046322 A1 | 2/2014 | Callas et al. | |
| 2014/0052126 A1 | 2/2014 | Long et al. | |
| 2014/0081256 A1 | 3/2014 | Carmel et al. | |
| 2014/0228835 A1 | 8/2014 | Mielekamp et al. | |
| 2014/0277219 A1 | 9/2014 | Nanda | |
| 2014/0336638 A1 | 11/2014 | Deem et al. | |
| 2014/0358066 A1 | 12/2014 | Nuccitelli et al. | |
| 2015/0032100 A1 | 1/2015 | Coulson et al. | |
| 2015/0065946 A1 | 3/2015 | Gehl et al. | |
| 2015/0272657 A1 | 10/2015 | Yates et al. | |
| 2016/0066977 A1 | 3/2016 | Neal, II et al. | |
| 2017/0033686 A1 | 2/2017 | Cadilhon | |
| 2017/0245928 A1 | 8/2017 | Xiao et al. | |
| 2017/0246455 A1 | 8/2017 | Athos et al. | |
| 2017/0319851 A1 | 11/2017 | Athos et al. | |
| 2017/0326361 A1 | 11/2017 | Kreis | |
| 2017/0360504 A1 | 12/2017 | Nuccitelli et al. | |
| 2018/0078755 A1 | 3/2018 | Kreis | |
| 2018/0110557 A1 | 4/2018 | Muratori et al. | |
| 2018/0154142 A1 | 6/2018 | Muratori et al. | |

FOREIGN PATENT DOCUMENTS

| | | | |
|---|---|---|---|
| WO | 2005/115536 A1 | 12/2005 | |
| WO | 2007/030415 A1 | 3/2007 | |
| WO | 2008/034103 A1 | 3/2008 | |
| WO | 2011/109141 A1 | 9/2011 | |
| WO | 2011/146498 A2 | 11/2011 | |
| WO | WO-2011146498 A2 * | 11/2011 | .............. H02M 3/07 |
| WO | 2012/076844 A1 | 6/2012 | |
| WO | 2014/060854 A1 | 4/2014 | |
| WO | 2016/089781 A1 | 6/2016 | |
| WO | 2017/151260 A1 | 9/2017 | |
| WO | 2017/151261 A1 | 9/2017 | |
| WO | 2017/200954 A1 | 11/2017 | |
| WO | 2017/201394 A1 | 11/2017 | |
| WO | 2018/053539 A1 | 3/2018 | |
| WO | 2018/075946 A1 | 4/2018 | |
| WO | 2018/089506 A1 | 5/2018 | |

OTHER PUBLICATIONS

JP-2018561184—JPO-191203—Notice of Reasons_for_Refusal—English translation.
KR-10-2018-7024287—KIPO-200316—Office Action English Translation.

(56) References Cited

OTHER PUBLICATIONS

Anand et al., "Adaptive Immune Response to Nano-Pulse Stimulation (NPS), Nov. 11, 2016, Poster presentation at the 31st Annual Meeting and Associated Programs of the Society for Immunotherapy of Cancer," Retrieved from the Internet: URL: http://pulsebiosciences.com/assets/Pulse%20AIR%20poster.pdf, retrieved on Mar. 13, 2018.
Anand et al., "Nano-Pulse Electro-Signaling treatment of murine tumors significantly reduces the percentage of regulatory T cells in the treated tumor," Journal for Immunotherapy of Cancer: 31st Annual Meeting and Associated Programs of the Society for Immunotherapy of Cancer (SITC 2016), Part Two, National Harbor, MD, USA Nov. 16, 2016, p. 214.
Australian Application No. 2017225297, Australian First Examination Report, dated Mar. 7, 2019, 6 pages.
Baker et al., "Stacking Power MOSFETs for use in High Speed Instrumentation," Rev. Sci. Instrum., American Institute of Physics, Dec. 1992, vol. 63, No. 12, pp. 5799-5801.
Beebe, S. J., "Hepatocellular carcinoma ablation and possible immunity in the age of nanosecond pulsed electric fields," Journal of Hepatocellular Carcioma, May 2015, No. 2, pp. 49-55.
Bhosale et al., "Design and Simulation of 50 kV, 50 A Solid State Marx Generator," International Conference on Magnetics, Machines & Drives (AICERA—2014 iCMMD), IEEE 2014, pp. 1-5.
Carey et al., "Marx Generator Design and Performance," Applied Physical Electronics, L.C., 2002, 4 pages.
Casey et al., "Solid-State Marx Bank Modulator for the Next Generation Linear Collider," Conference Record of the 26$^{th}$ International Power Modulator Symposium and 2004 High Voltage Workshop (PMC), San Francisco, California, May 23-26, 2004, IEEE 2004, pp. 257-260.
Cook et al., "Design and Testing of a Fast, 50 kV Solid-State Kicker Pulser," IEEE 2002, pp. 106-109.
Garon et al. "In Vitro and In Vivo Evaluation and a Case Report of Intense Nanosecond Pulsed Electric Field as a Local Therapy for Human Malignancies", Int. J. Cancer, vol. 121, 2007, pp. 675-682.
Gaudreau et al., "Solid-State Pulsed Power Systems for the Next Linear Collider," IEEE 2002, pp. 298-301.
Gundersen et al. "Nanosecond Pulse Generator Using a Fast Recovery Diode", IEEE 26.sup.th Power Modulator Conference, 2004, pp. 603-606.
International Application No. PCT/US15/63025, International Search Report and Written Opinion dated Apr. 21, 2016, 9 pages.
International Application No. PCT/US2017/015881, Invitation to Pay Additional Fees and, Where Applicable, Protest Fee, dated Mar. 15, 2017, 2 pages.
Japanese Application No. 2018-561184, Office Action dated Jul. 23, 2019, 3 pages.
Jiang et al., "Marx Generator Using Power Mosfets," IEEE 2009, pp. 408-410.
Kirbie et al., "An All Solid State Pulse Power Source for High PRF Induction Acceslerators," IEEE 1998, pp. 6-11.
Krasnykh et al., "A Solid State Marx Type Modulator for Driving a TWT," Conference Record of the 24$^{th}$ International Power Modulator Symposium 2000, p. 209-211.
Mcdaniel et al., "Nanosecond pulsed electric field treatment of tumor cell lines triggers immunogenic cell death (ICD)," Nov. 11, 2016, Poster presentation at the 31st Annual Meeting and Associated Programs of the Society for Immunotherapy of Cancer (SITC 2016), National Harbor, MD, USA; Retrieved from the Internet: URL: http://pulsebiosciences.com/assets/Pulse%20ICD%20poster.pdf, retrieved on Mar. 13, 2018.
Mcdaniel et al., "P329 Nanosecond pulsed electric field treatment of tumor cell lines triggers immunogenic cell death (ICD)," Journal for ImmunoTherapy of Cancer: 31st Annual Meeting and Associated Programs of the Society for Immunotherapy of Cancer (SITC 2016): part two: National Harbor, MD, USA, Nov. 16, 2016, p. 175.
Nader Yatim et al., "RIPK1 and NF-κB signaling in dying cells determines cross-priming of CD8$^+$ T cells," Science, Oct. 2015, vol. 350, Issue 6258, pp. 328-335, sciencemag.org.
Okamura et al. "Development of the High Repetitive Impulse Voltage Generator Using Semiconductor Switches," IEEE 1999, pp. 807-810.
PCT/US2015/063025, "International Search Report" dated Apr. 21, 2016, 4 pages.
PCT/US2017//032744, "International Search Report" dated Jul. 21, 2017, 2 pages.
PCT/US2017/015881, "International Search Report" dated May 25, 2017, 4 pages.
PCT/US2017/015884, "International Search Report," dated Apr. 21, 2017, 3 pages.
PCT/US2017/052340, "International Search Report", dated Jan. 8, 2018, 3 pages.
PCT/US2017/057698, "International Search Report" dated Feb. 27, 2018, 3 pages.
PCT/US2017/060654, "International Search Report" dated Feb. 27, 2018, 6 pages.
PCT/US2017/064685, "International Search Report" dated Mar. 22, 2018, 5 pages.
PCT/US2018/019213, "International Search Report" dated May 22, 2018, 4 pages.
Redondo et al., "Solid-State Marx Generator Design with an Energy Recovery Reset Circuit for Output Transformer Association," Power Electronics Specialists Conference, IEEE, 2007, 5 pages.
Richter-Sand et al., "Marx-Stacked IGBT Modulators for High Voltage, High Power Applications," IEEE 2002, pp. 390-393.
Sack et al., "Design Considerations for a Fast Stacked-MOSFET Switch," IEEE Transactions on Plasma Science, vol. 41, No. 10, Oct. 2013, pp. 2630-2636.
Tang et al. "Diode Opening Switch Based Nanosecond High Voltage Pulse Generators for Biological and Medical Applications", IEEE Transactions on Dielectrics and Electrical Insulation, vol. 14, No. 4, 2007, pp. 878-883.
U.S. Appl. No. 15/148,344, Final Office Action dated Aug. 9, 2019, 14 pages.
U.S. Appl. No. 15/148,344, Non-final Office Action dated Feb. 7, 2019, 12 pages.
U.S. Appl. No. 15/148,344, Notice of Allowance and Fee(s) Due, dated Oct. 17, 2019, 7 pages.
Wang et al. "Solid-State High Voltage Nanosecond Pulse Generator," IEEE Pulsed Power Conference, 2005, pp. 1199-1202.
Yao et al., "FPGA-Controlled All-Solid-State Nanosecond Pulse Generator for Biological Applications," IEEE Transactions on Plasma Science, vol. 40, No. 10, Oct. 2012, pp. 2366-2372.
European Application No. 17760444.4, Extended Search Report and Opinion, dated Oct. 15, 2019, 7 pages.
Canadian Application No. 3,015,756, Office Action dated Jun. 17, 2019, 6 pages.
Grekhov et al., "High-Power Semiconductor-Based Nano and Subnanosecond Pulse Generator With a Low Delay Time," IEEE Transactions on Plasma Science, Aug. 2005, vol. 33, No. 4, pp. 1240-1244.

* cited by examiner

HIGH-VOLTAGE ANALOG CIRCUIT PULSER

CROSS-REFERENCES TO RELATED APPLICATIONS

This application claims the benefit of and priority to U.S. patent application Ser. No. 15/148,344, filed May 6, 2016, entitled "HIGH-VOLTAGE ANALOG CIRCUIT PULSER WITH FEEDBACK CONTROL," which further claims the benefit of and priority to U.S. provisional application No. 62/301,477, filed Feb. 29, 2016, entitled "HIGH-VOLTAGE ANALOG CIRCUIT PULSER," each of which are incorporated herein by reference in their entirety for all purposes.

BACKGROUND

1. Field of the Invention

The present application generally relates to electrical pulse techniques including circuits and systems for generating electric pulses, including the use of an energy-accumulating element discharged through a load by a relatively low voltage transistor and for controlling the discharge. Specifically, the pulse techniques are used for generating variable duration nanosecond pulsed electric fields (nsPEF) for electrotherapy.

2. Description of the Related Art

Surgical excision of a tumor can result in an infection and leave a scar. Furthermore, if there are more tumors, every cancerous tumor should be identified and individually excised by a surgeon. This can be time consuming and expensive, not to mention uncomfortable for patients.

Cancerous tumors that are internal to a patient may be especially difficult to remove, let alone detect and treat. Many patients' lives are turned upside down by the discovery of cancer in their bodies, sometimes which have formed relatively large tumors before being detected.

A "nanosecond pulsed electric field," sometimes abbreviated as nsPEF, includes an electric field with a sub-microsecond pulse width of between 0.1 nanoseconds (ns) and 1000 nanoseconds, or as otherwise known in the art. It is sometimes referred to as sub-microsecond pulsed electric field. NsPEFs often have high peak voltages, such as 10 kilovolts per centimeter (kV/cm), 20 kV/cm, to 500 kV/cm. Treatment of biological cells with nsPEF technology often uses a multitude of periodic pulses at a frequency ranging from 0.1 per second (Hz) to 10,000 Hz.

NsPEFs have been found to trigger apoptosis in cancerous tumors. Selective treatment of such tumors with nsPEFs can induce apoptosis within the tumor cells without substantially affecting normal cells in the surrounding tissue due to its non-thermal nature.

An example of nsPEF applied to biological cells is shown and described in U.S. Pat. No. 6,326,177 (to Schoenbach et al.), which is incorporated herein by reference in its entirety for all purposes.

The use of nsPEF for the treatment of tumors is a relatively new field. There exists a need for a device with better control over electrical characteristics for safe and effective studies and treatments of cancer in human subjects.

BRIEF SUMMARY

Generally, a nanosecond pulsed electric field (nsPEF) generator is disclosed that incorporates a feedback control system for compensating or adjusting one or more characteristics of the nsPEF pulses generated. For example, one or more of supply voltage, pulse width, number of pulses, frequency of pulses, duty cycle, or another characteristic may be adjusted in response to a measured parameter. For example, one or more characteristics may be adjusted in response to a measurement of one or more of current, voltage, temperature, or another parameter.

To generate high voltage short duration pulses for nsPEF treatments a nanosecond pulsed electric field (nsPEF) generator is used. The pulses generated are preferably controllable at least in one or more aspects, such as duration, amplitude, rise/fall time, and affect on temperature of the treated tissue.

One inventive aspect is a sub-microsecond pulsed electric field generator. The field generator includes a controller, configured to generate a power supply control signal and to generate a pulse generator control signal, and a power supply, configured to receive the power supply control signal and configured to generate one or more power voltages based in part on the received power supply control signal. The field generator also includes a pulse generator configured to receive the one or more power voltages and the pulse generator control signal, and to generate one or more pulses based in part on the one or more power voltages received from the power supply and based in part on the pulse generator control signal received from the controller. The controller is configured to receive one or more feedback signals representing a value of a characteristic of or a result of the pulses and to generate at least one of the power supply control signal and the pulse generator control signal based partly on the received one or more feedback signals.

Another inventive aspect is a method of generating one or more sub-microsecond pulsed electric field pulses. The method includes generating a power supply control signal with a controller, generating a pulse generator control signal with the controller, and receiving the one or more power supply control signals at a power supply. The method also includes generating one or more power voltages based in part on the power supply control signal with the power supply, receiving the one or more power voltages and the pulse generator control signal at a pulse generator, and, with the pulse generator, generating one or more pulses based in part on the one or more power voltages received from the power supply and based in part on the pulse generator control signal received from the controller. The method also includes receiving, at the controller, one or more feedback signals representing a value of a characteristic of or a result of the pulses. In addition, at least one of the power supply control signal and the pulse generator control signal is generated by the controller based partly on the received one or more feedback signals.

Another inventive aspect is a sub-microsecond pulsed electric field generator. The field generator includes a controller, configured to generate a power supply control signal and to generate a pulse generator control signal at a controller output, and a power supply, including a power supply input configured to receive the power supply control signal, where the power supply is configured to generate one or more power voltages at one or more corresponding power supply outputs, and where the one or more power voltages is generated based in part on the received power supply control signal. The field generator also includes a pulse generator, including a plurality of pulse generator inputs configured to receive the one or more power voltages and the pulse generator control signal, where the pulse generator is configured to generate one or more pulses based in part on the one or more power voltages received from the power supply and based in part on the pulse generator control signal received from the controller. In addition, the controller includes a feedback input configured to receive one or more feedback signals representing a value of a characteristic of or a result of the pulses, and the controller is configured to generate at least one of the power supply control signal and the pulse generator control signal based partly on the received one or more feedback signals.

DETAILED DESCRIPTION

It has been shown that nsPEF treatments can be used to cause cancerous tumor cells to undergo apoptosis, a programmed cell death. Tests have shown that tumors can shrink to nonexistence after treatment. No drugs may be necessary. It has also been shown that the subject's immune system may be stimulated to attack all similar tumor cells, including those of tumors that are not within the nsPEF-treated tumor.

A "tumor" includes any neoplasm or abnormal, unwanted growth of tissue on or within a subject, or as otherwise known in the art. A tumor can include a collection of one or more cells exhibiting abnormal growth. There are many types of tumors. A malignant tumor is cancerous, a pre-malignant tumor is precancerous, and a benign tumor is noncancerous. Examples of tumors include a benign prostatic hyperplasia (BPH), uterine fibroid, pancreatic carcinoma, liver carcinoma, kidney carcinoma, colon carcinoma, pre-basal cell carcinoma, and tissue associated with Barrett's esophagus.

A "disease" includes any abnormal condition in or on a subject that is associated with abnormal, uncontrolled growths of tissue, including those that are cancerous, precancerous, and benign, or other diseases as known in the art.

"Apoptosis" of a tumor or cell includes an orderly, programmed cell death, or as otherwise known in the art.

"Immunogenic apoptosis" of a tumor or cell includes a programmed cell death that is followed by an immune system response, or as otherwise known in the art. The immune system response is thought to be engaged when the apoptotic cells express calreticulin or another antigen on their surfaces, which stimulates dendritic cells to engulf, consume, or otherwise commit phagocytosis of the targeted cells leading to the consequent activation of a specific T cell response against the target tumor or cell.

Pulse lengths of between 10 and 900 nanoseconds for nsPEF have been particularly studied to be effective in stimulating an immune response. Pulse lengths of about 100 nanoseconds are of particular interest in that they are long enough to carry sufficient energy to be effective at low pulse numbers but short enough to be effective in the manner desired.

A time of "about" a certain number of nanoseconds includes times within a tolerance of ±1%, 2%, 3%, 4%, 5%, 7.5%, 10%, 15%, 20%, 25% or other percentages, or fixed tolerances, such as ±0.1, ±0.2, ±0.3, ±0.4, ±0.5, ±0.7, ±1.0, ±2.0, ±3.0, ±4.0±5.0, ±7.0, ±10, ±15, ±20, ±25, ±30, ±40, ±50, ±75 ns, or other tolerances as acceptable in the art in conformance with the effectivity of the time period.

Immune system biomarkers can be measured before and/or after nsPEF treatment in order to confirm that the immune response has been triggered in a patient. Further, nsPEF treatment can be paired with a CD47-blocking antibody treatment to better train CD8+T cells (i.e., cytotoxic T cells) for attacking the cancer.

Figure 1:
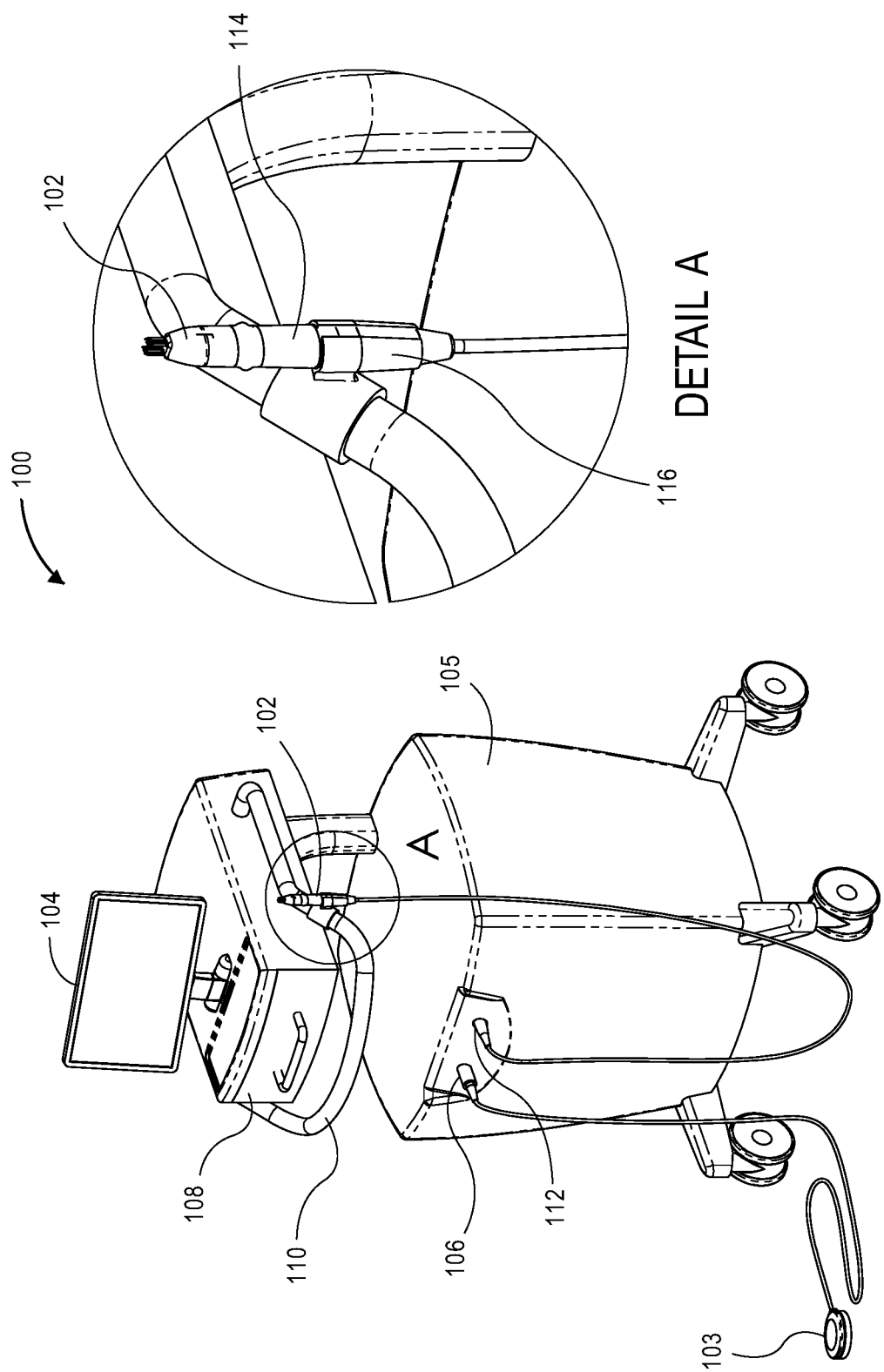
FIG. 1 illustrates a nanosecond pulse generator apparatus in accordance with an embodiment.

FIG. 1 illustrates a nanosecond pulse generator system in accordance with an embodiment. NsPEF system 100 includes electrode 102, footswitch 103, and interface 104. Footswitch 103 is connected to housing 105 and the electronic components therein through connector 106. Electrode 102 is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold electrode 102 at its handle portion 114.

A human operator inputs a number of pulses, amplitude, pulse duration, and frequency information, for example, into a numeric keypad or a touch screen of interface 104. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

Figure 2:
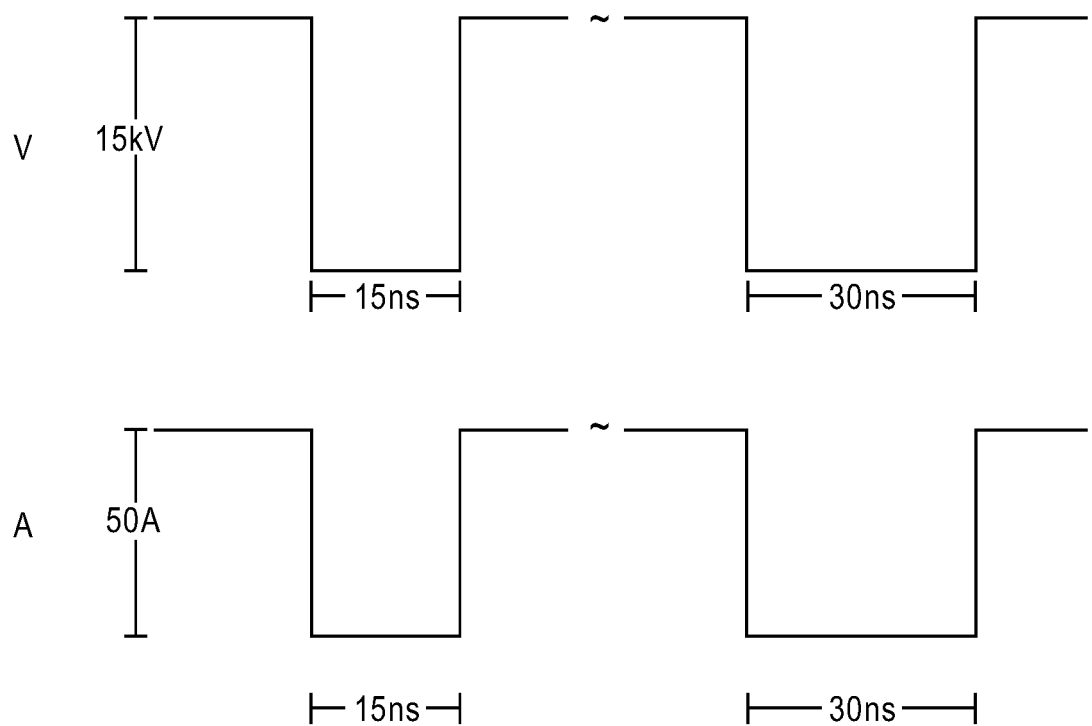
FIG. 2 illustrates a pulse profile for both voltage and current in accordance with an embodiment.

FIG. 2 illustrates a pulse profile for both voltage and current in accordance with an embodiment. Output from the nsPEF system 100 with voltage on the top of the figure and current on the bottom for a first and second pulses. The first pulse has an amplitude of about 15 kV, a current of about 50 A, and a duration of about 15 ns. The second pulse has an amplitude of about 15 kV, a current of about 50 A, and a duration of about 30 ns. If such a pulse had been delivered on suction electrodes having 4 mm between the plates, the pulse generator would have delivered a pulse of about 50 A and 37.5 kV/cm. Given a voltage, current depends heavily on the electrode type and tissue resistance.

While FIG. 2 illustrates a specific example, other pulse profiles may also be generated. For example, in some embodiments, rise and/or fall times for pulses may be less than 20 ns, about 20 ns, about 25 ns, about 30 ns, about 40 ns, about 50 ns, about 60 ns, about 75 ns, or greater than 75 ns. In some embodiments, the pulse voltage may be less than 5 kV, about 5 kV, about 10 kV, about 15 kV, about 20 kV, about 25 kV, about 30 kV, or greater than 30 kV. In some embodiments, the current may be less than 10 A, about 10 A, about 25 A, about 40 A, about 50 A, about 60 A, about 75 A, about 100 A, about 125 A, about 150 A, about 175 A, about 200 A, or more than 200 A. In some embodiments, the pulse duration may be less than 10 ns, about 10 ns, about 15 ns, about 20 ns, about 25 ns, about 30 ns, about 40 ns, about 50 ns, about 60 ns, about 75 ns, about 100 ns, about 125 ns, about 150 ns, about 175 ns, about 200 ns, about 300 ns, about 400 ns, about 500 ns, about 750 ns, about 1 µs, about 2 µs, about 3 µs, about 4 µs, about 5 µs, or greater than 5 µs.

Figure 3:
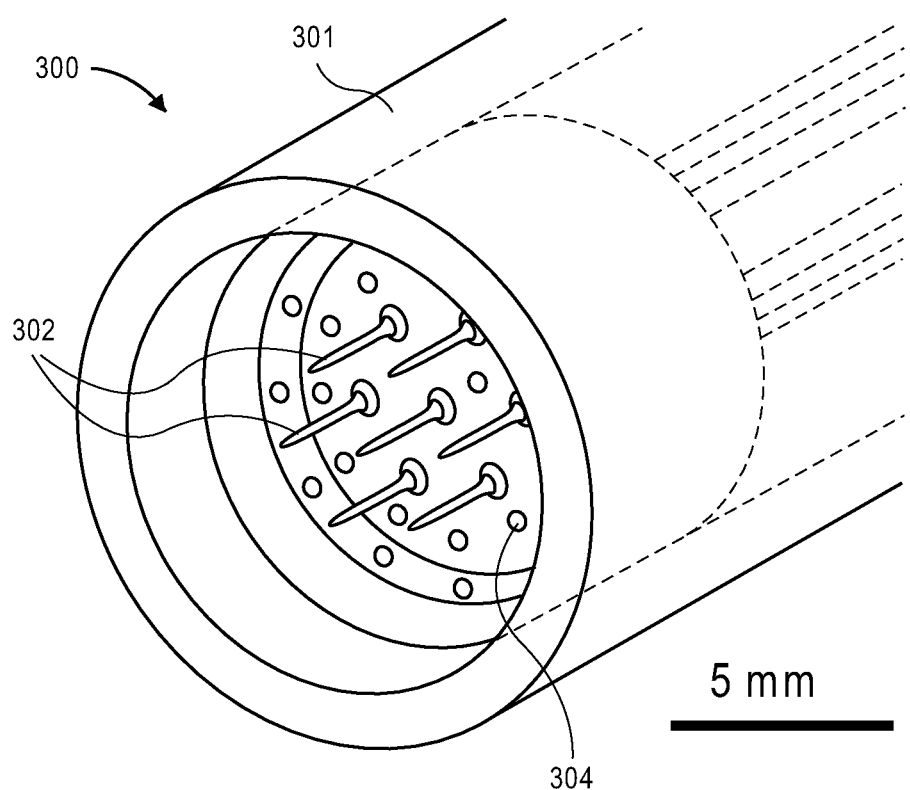
FIG. 3 illustrates a perspective view of a seven-needle electrode in accordance with an embodiment.

FIG. 3 illustrates a perspective view of a seven-needle suction electrode in accordance with an embodiment. In electrode 300, sheath 301 surrounds seven sharp electrodes 302 with an broad opening at a distal end. When the open end is placed against a tumor, air is evacuated from the resulting chamber through vacuum holes 304 to draw the entire tumor or a portion thereof into the chamber. The tumor is drawn so that one or more of the electrodes preferably penetrates the tumor. Sharp ends of the electrodes are configured to pierce the tumor. The center electrode may be at one polarity, and the outer six electrodes may be at the opposite polarity. Nanopulses electric fields can then be precisely applied to the tumor using nsPEF system 100 (see FIG. 1).

The electrodes can be apposed, one of each positive and negative pair of electrodes on one side of a tumor and the other electrode of the pair on an opposing side of the tumor. Opposing sides of a tumor can include areas outside or within a tumor, such as if a needle electrode pierces a portion of the tumor.

Figure 4:
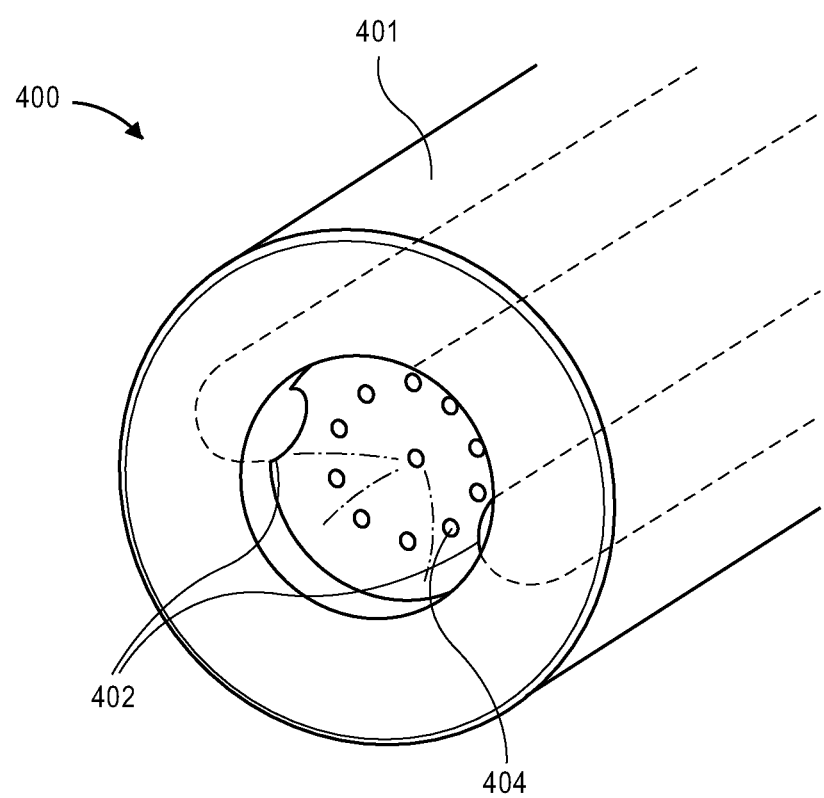
FIG. 4 illustrates a perspective view of a two-pole electrode in accordance with an embodiment.

FIG. 4 illustrates a two-pole suction electrode in accordance with an embodiment. In electrode device 400, sheath 401 surrounds two broad electrodes 402 on opposite sides of a chamber. When air is evacuated through vacuum holes 404 and a tumor is pulled within the chamber, the opposing electrodes apply nsPEF pulses to the tumor.

The nature of the electrode used mainly depends upon the shape of the tumor. Its physical size and stiffness can also be taken into account in selection of a particular electrode type.

U.S. Pat. No. 8,688,227 B2 (to Nuccitelli et al.) discloses other suction electrode-based medical instruments and systems for therapeutic electrotherapy, and it is hereby incorporated by reference.

If there are multiple tumors in a subject, a surgeon can select a single tumor to treat based on the tumor's compatibility with electrodes. For example, a tumor that is adjacent to a stomach wall may be more easily accessible than one adjacent a spine or the brain. Because a nsPEF pulse is preferably applied so that the electric field transits through as much tumor mass as possible while minimizing the mass of non-tumor cells that are affected, a clear path to two opposed 'poles' of a tumor may also be a selection criterion.

For tumors on or just underneath the skin of subject, needle electrodes can be used percutaneously. For locations deeper within a subject, a retractable electrode can fit into a gastroscope, bronchoscope, colonoscope, or other endoscope or laparoscope. For example, a tumor in a patient's colon can be accessed and treated using an electrode within a colonoscope.

Barrett's esophagus, in which portions of tissue lining a patient's esophagus are damaged, may be treated using an electrode placed on an inflatable balloon.

Embodiments of nanosecond pulsed power generators produce electric pulses in the range of single nanoseconds to single microseconds. The pulses are created by rapid release of energy stored in, for example, a capacitive or inductive energy reservoir to a load in a period that is generally much shorter than the charging time of the energy reservoir.

Conventional capacitive-type pulsed generators include pulse forming networks, which provide fixed pulse duration and impedance. With prior knowledge of a load's resistance, a pulse forming network with impedance that matches the load can be used. But for broader applications, especially when the load resistance is unknown, it is desirable to have a pulse generator with a flexibility of impedance matching and variation of pulse duration. Such flexibility can be implemented by switching a capacitor with a controllable switch. In this case, the capacitor can be regarded as a "voltage source" and can adapt to various load resistance. The switched pulse amplitude can then have the same voltage as the voltage of the capacitor. The pulse width is accordingly determined by the switch "on" time.

The selection of switches in nanosecond pulse generators is limited because of the high voltages, high currents, and fast switching times involved.

Spark gap switches, typically used in pulsed power technology, are capable of switching high voltages and conducting high currents. But they can only be turned on, and stopping the current flow in the middle of conduction is impossible. Besides spark gaps, other types of high voltage, high power switches are available, such as: magnetic switches, vacuum switches (Thyratrons for example), and certain high-voltage semiconductor switches.

Magnetic switches, relying on the saturation of magnetic core, change from high impedance to low impedance in the circuit. They can be turned on above a certain current threshold but will not be turned off until all the current is depleted by the load.

Vacuum switches are a good option for high voltage and high repletion rate operation, but similar to magnetic switches, they also can be only turned on, but cannot be turned off at a predetermined time.

Some types of high-voltage semi-conductor switches may also be considered. Thyristors and insulated gate bipolar transistors (IGBTs) may, in some embodiments be used. However, the turn-on times of Thyristors and IGBTs limit their usefulness.

Metal-oxide-semiconductor field-effect transistors (MOSFETs) have insufficient maximum drain to source voltage ratings (e.g. <1 kV) and insufficient maximum drain to source current ratings (e.g. <50 A) to be used in conventional pulse generator architectures to produce the voltage and current necessary for the applications discussed herein. If they were used, a large number of stages would be needed in order to produce high-amplitude output voltages. However, in conventional Marx generator architectures with a large number of stages, the Marx generator goes into an underdamped mode instead of a critically damped mode, resulting in loss in overshoot. As a result, the overall voltage efficiency decreases. For example, a voltage efficiency of a Marx generator may be 80% at 5 stages but decrease to 50% at 20 stages.

Furthermore, as the number of stages is increased, the impedance of the Marx generator also increases. This reduces the total energy deliverable to the load. This is particularly unfavorable for driving low impedance loads and long pulses.

In addition, the charging losses in the charging resistors also increases with the increased number of stages. As a result, such Marx generators are unsuitable for high repetition rate operation.

Therefore, in order to produce high voltage pulses, simply increasing the number of stages will cause a series of problems, including low efficiency, high impedance, etc. Because there is a tradeoff between the number of the stages and the actual output voltage, using conventional Marx generators cannot produce high voltage pulses which are sufficient for the applications discussed herein.

Some embodiments of this disclosure include a tunable, high voltage, nanosecond pulse generator. The switches may be power MOSFETs, which may, for example, be rated for a voltage of 1 kV and current of up to 30 A. In some embodiments, the switches power MOSFETs rated for a voltage of 1 kV and current of up to continuous 90 A and more than 200 A peak. Voltage is scaled up by a Marx-switch stack hybrid circuit. In each Marx generator stage, a particularly configured stack of MOSFETs is used. As a result, the charging voltage for each stage is greater than the rated maximum for a single switch.

A technical advantage of the configuration is that the overall output voltage can be increased with just a few stages (e.g. <=5). As a result, the problems discussed above with Marx generators having a large number of stages are avoided and high efficiency, low impedance, and large variability in the pulse duration can be achieved.

Such an architecture also allows much easier control as only one trigger circuit may be needed for each stage. One additional benefit is that the pulse generator has low impedance, so it will be able to drive various loads with high current and extended pulse duration. The scaling up of the current is implemented by combining multiple Marx-switch stack circuits in parallel. The pulse duration is controlled by the closing and opening of the switch stack switches.

Figure 5:
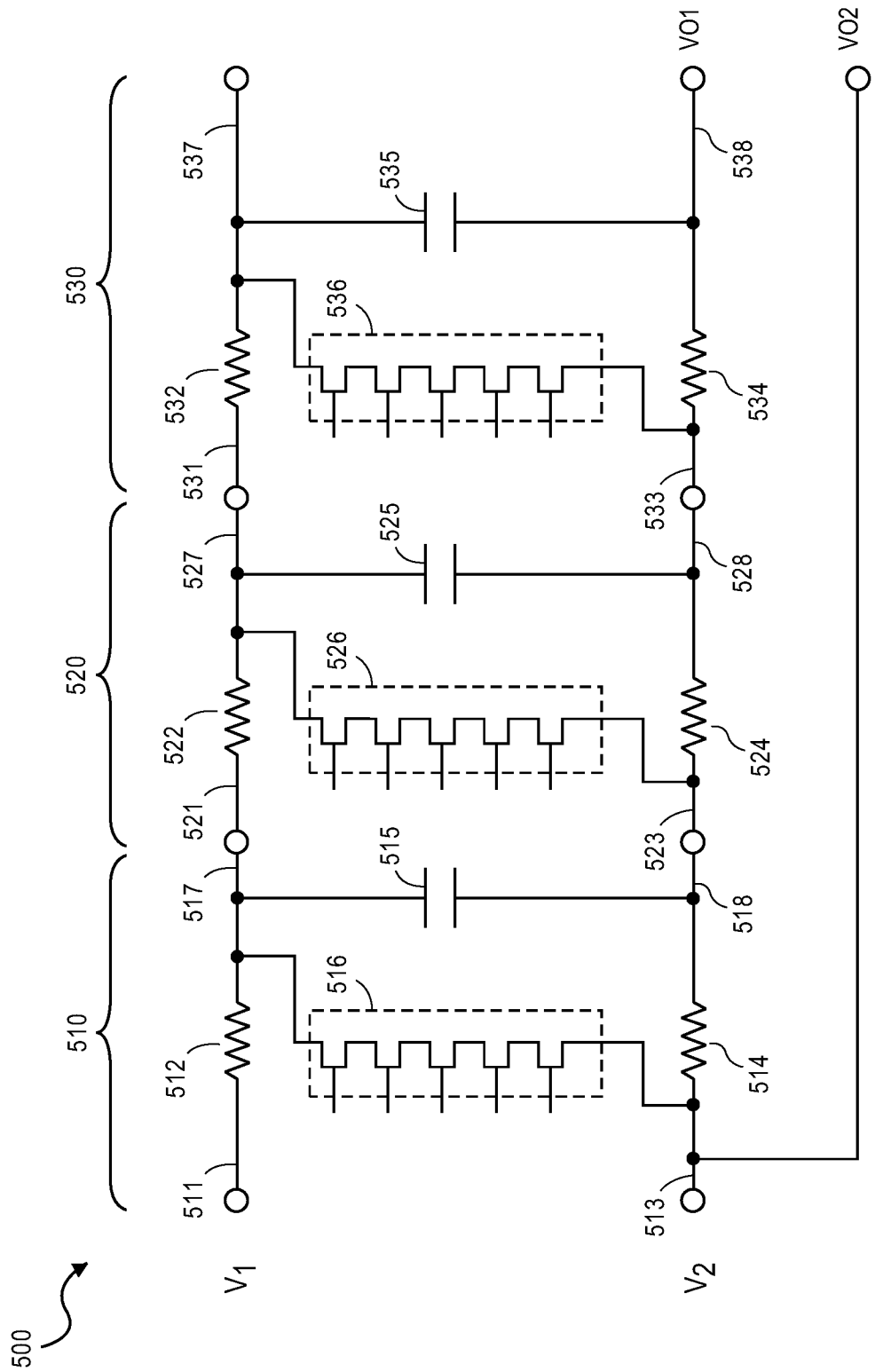
FIG. 5 is an electrical schematic of a pulse generator in accordance with an embodiment.

FIG. 5 illustrates a pulse generator circuit 500 which may be used inside nsPEF system 100 of FIG. 1. Pulse generator circuit 500 illustrates a panel comprising a Marx generator switched by three switch stacks. The nsPEF system can have a single pulse generator circuit panel. In some embodiments, a nsPEF system includes multiple panels in parallel.

Circuit 500 includes three stages—510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second input voltage input terminals 511 and 513 and first and second voltage output terminals 517 and 518. Stage 520 has first and second input voltage input terminals 521 and 523, and first and second voltage output terminals 527 and 528. Stage 530 has first and second input voltage input terminals 531 and 533, and first and second voltage output terminals 537 and 538.

The first and second voltage input terminals 511 and 513 of stage 510 are respectively connected to first and second power supply input terminals V1 and V2. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

Pulse generator circuit 500 operates in a charge mode, and in a discharge mode. During the charge mode, described below with reference to FIG. 6A in more detail, capacitors 515, 525, and 535 are charged by current received from the first and second power supply input terminals V1 and V2. During the discharge mode, described below with reference to FIG. 6B in more detail, capacitors 515, 525, and 535 are discharged to provide a current to a load (not shown) connected across first and second power output terminals VO1 and VO2.

Figure 6A:
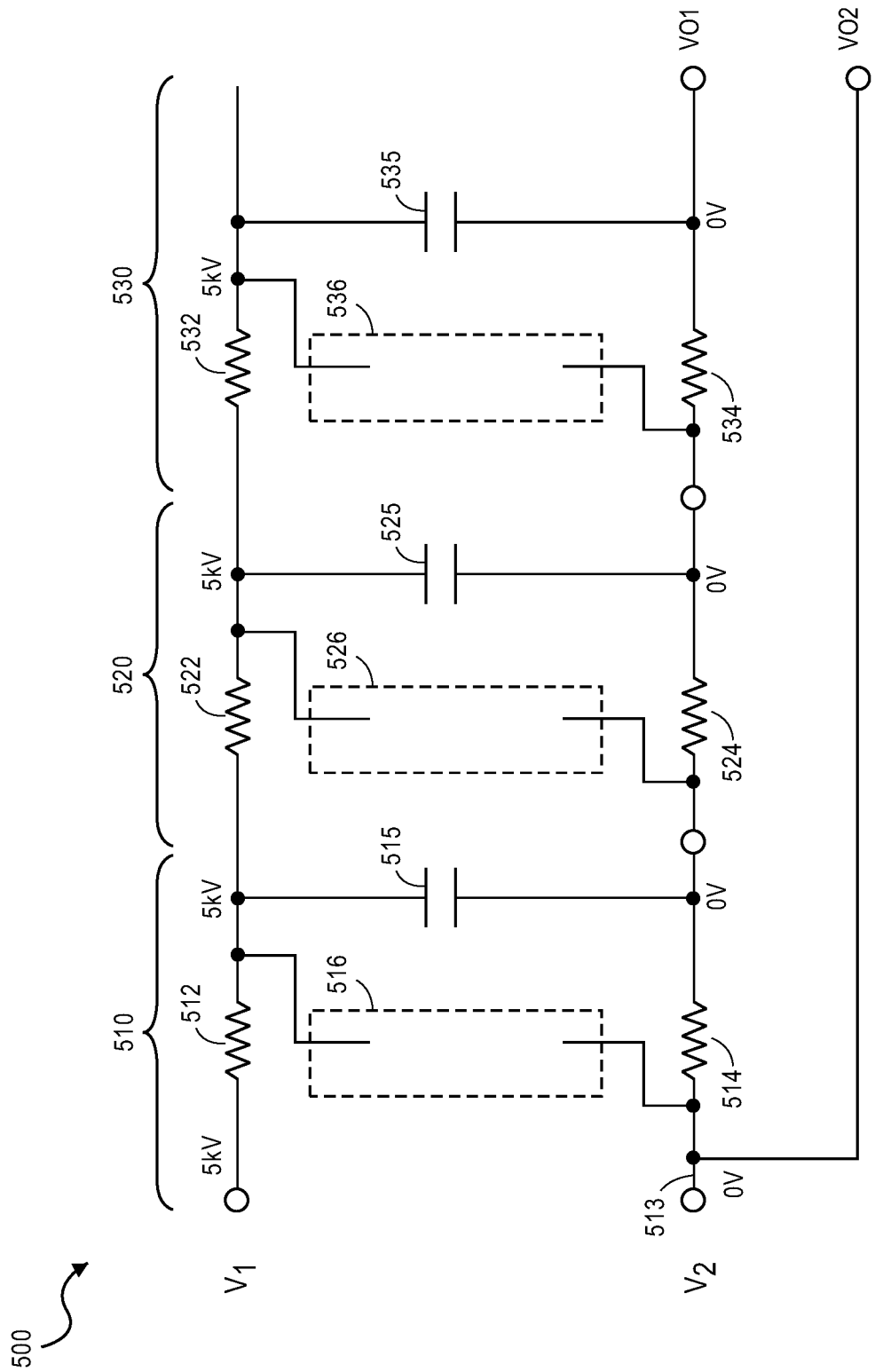
FIG. 6A is a schematic illustrating the pulse generator shown in FIG. 5 during charge mode.

FIG. 6A illustrates pulse generator circuit 500 during charge mode. First and second input voltages are respectively applied to first and second power supply input terminals V1 and V2 while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 6A. During the charge mode, each of capacitors 515, 525, and 535 are charged by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0V. In such an example, each of the capacitors 515, 525, and 535 is charged to or toward a voltage equal to 5 kV. In some embodiments, the difference between the first and second input voltages is limited to be less than 10 kV.

Figure 6B:
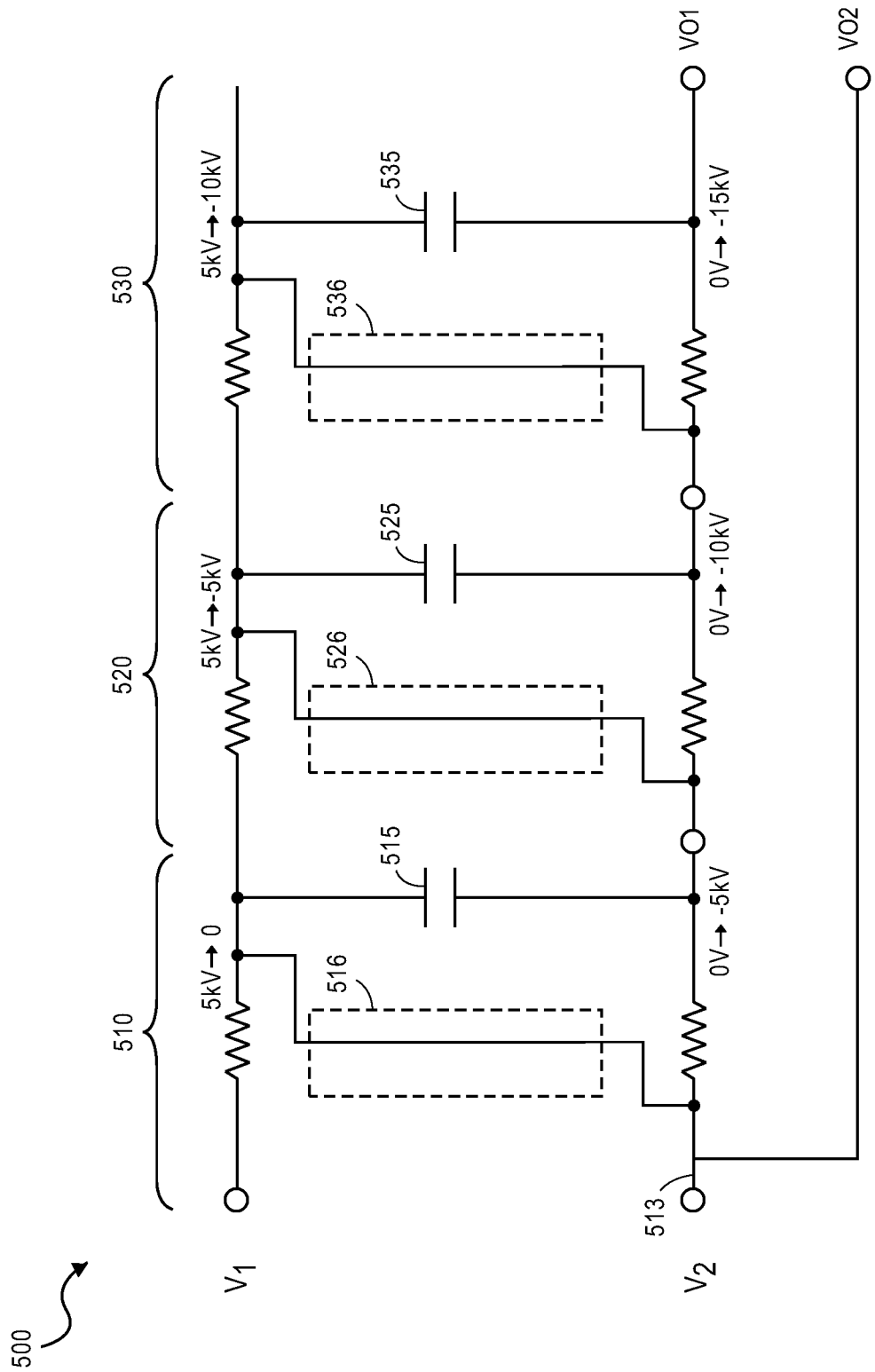
FIG. 6B is a schematic illustrating the pulse generator shown in FIG. 5 during discharge mode.

FIG. 6B illustrates pulse generator circuit 500 during discharge mode. First power supply input terminal V1 may be disconnected from the first input voltage. In some embodiments, first power supply input terminal V1 remains connected to the first input voltage. Second power supply input terminal V2 remains connected to the second input voltage. In addition, each of switch stacks 516, 526, and 536 are conductive or closed. Because each of switch stacks 516, 526, and 536 are closed, current flows therethrough, and they are represented as conductive wires in FIG. 6B. As a result, a low impedance electrical path from power supply input terminal V2 to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages.

Where the first and second input voltages are respectively 5 kV and 0V, a voltage difference of 15 kV is developed across the power output terminals VO1 and VO2.

Figure 7:
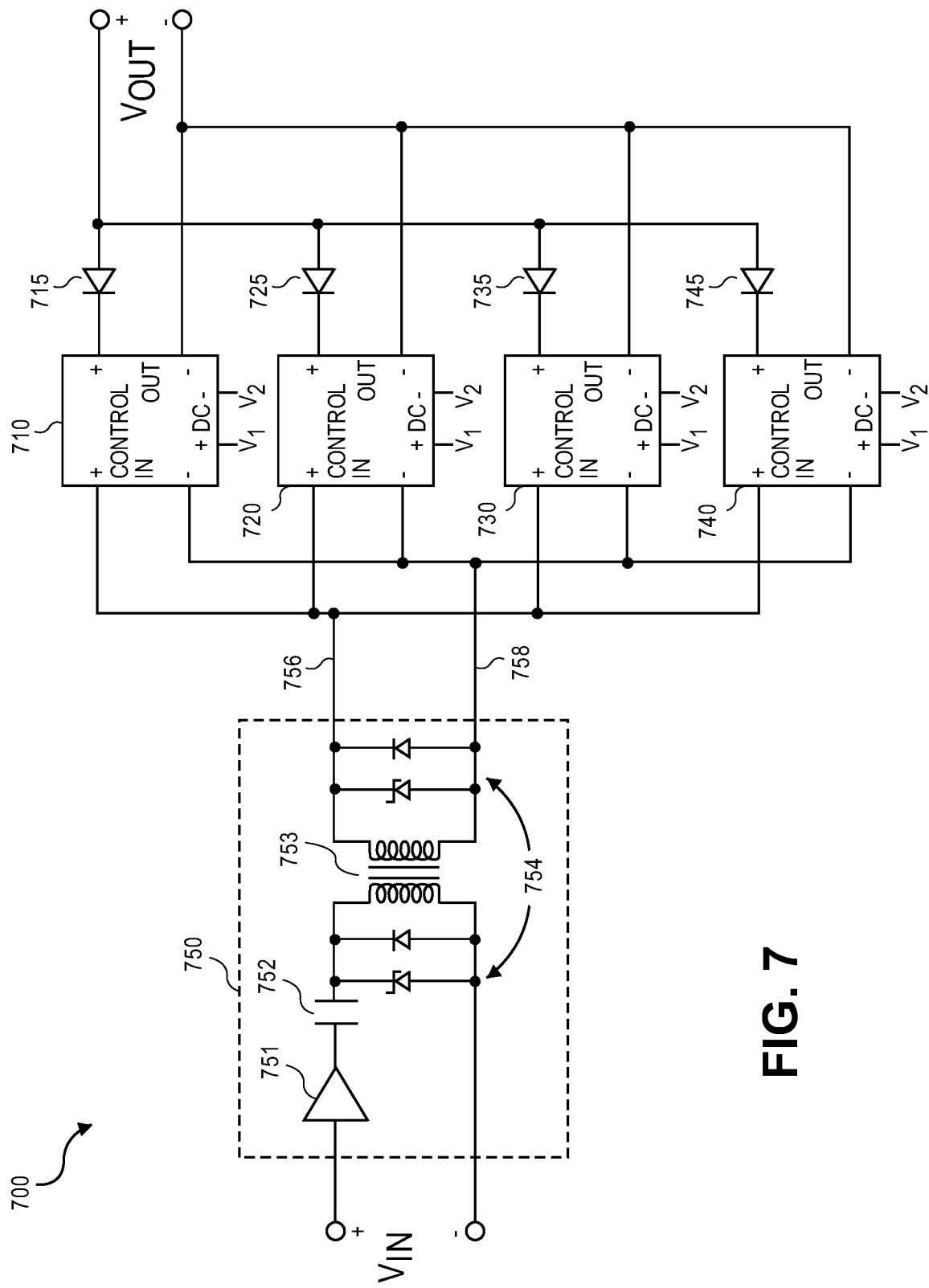
FIG. 7 is an electrical schematic of an assembly of pulse generator circuits.

FIG. 7 illustrates an alternative pulse generator circuit 700 which may be used inside nsPEF system 100 of FIG. 1. This pulse generator includes panels in parallel. The number of panels can be adjusted to allow the system to generate different amounts of current and power.

Pulse generator circuit 700 receives input pulses across input port Vin, and generates output pulses across output port Vout in response to the received input pulses.

Pulse generator circuit 700 includes multiple panels or pulse generator circuits 710, 720, 730, and 740. Pulse generator circuit 700 also includes driver 750. In this embodiment, four pulse generator circuits are used. In alternative embodiments, fewer or more pulse generator circuits are used. For example, in some embodiments, 2, 3, 5, 6, 7, 8, 9, 10 or another number of pulse generator circuits are used.

Each of the pulse generator circuits 710, 720, 730, and 740 may have characteristics similar to other pulse generator circuits discussed herein. For example, each the pulse generator circuits 710, 720, 730, and 740 may have characteristics similar to pulse generator circuit 500 discussed above with reference to FIGS. 5, 6A, and 6B.

Each of pulse generator circuits 710, 720, 730, and 740 has positive and negative DC input terminals, positive and negative control input terminals, and positive and negative output terminals, and is configured to generate output voltage pulses across the positive and negative output terminals in response to driving signal pulses applied across the positive and negative control input terminals. The output voltage pulses are also based on power voltages received across positive and negative DC power input terminals.

The driving signal pulses are generated across conductors 756 and 758 by driver 750, which includes amplifier circuit 751, capacitor 752, and transformer 753. In some embodiments, driver 750 also includes clamp circuits 754.

Driver 750 receives an input signal pulse at input port Vin and generates a driving signal pulse across conductors 756 and 758 in response to the input signal pulse. Amplifier circuit 751 receives the input signal pulse and drives transformer 753 through capacitor 752, which blocks low frequency and DC signals. In response to being driven by amplifier circuit 751, transformer 753 generates an output voltage pulse across conductors 756 and 758, such that the duration of the output voltage pulse is equal to or substantially equal (e.g. within 10% or 1%) to the duration of the input signal pulse at input port Vin.

In some embodiments, clamp circuits 754 are included at least to dampen potential signals, which may otherwise be caused by resonance. Clamp circuits 754 include parallel diodes, which provide a short-circuit path for any current reversal, and also clamp the maximum voltage across the components connected to the clamp circuits 754.

In some embodiments, transformer 753 has a 1:1 turns ratio. In alternative embodiments, a different turns ratio is used.

Each of pulse generator circuits 710, 720, 730, and 740 receives the voltage pulses from driver 750 across the positive and negative control input terminals and generates corresponding voltage pulses across the positive and negative output terminals in response to the received voltage pulses from driver 750. The voltage pulses generated across the positive and negative output terminals have durations which are equal to or substantially equal (e.g. within 10% or 1%) to the durations of the voltage pulses received from driver 750.

In this embodiment, the negative output terminals of pulse generator circuits 710, 720, 730, and 740 are directly connected to the negative Vout terminal of the output port Vout of pulse generator circuit 700. In addition, in this embodiment, the positive output terminals of pulse generator circuits 710, 720, 730, and 740 are respectively connected to the positive Vout terminal of the output port Vout of pulse generator circuit 700 through diodes 715, 725, 735, and 745. Diodes 715, 725, 735, and 745 decouple pulse generator circuits 710, 720, 730, and 740 from one another. As a consequence, interference and the associated pulse distortion that would otherwise occur is substantially eliminated. For example, diodes 715, 725, 735, and 745 prevent current from one of pulse generator circuits 710, 720, 730, and 740 to another of pulse generator circuits 710, 720, 730, and 740 if the switching is not perfectly synchronous. Diodes 715, 725, 735, and 745 also prevent current from flowing from the pulse generator circuits 710, 720, 730, and 740 while they are charging.

In this embodiment, diodes 715, 725, 735, and 745 each include a single diode. In alternative embodiments, diodes 715, 725, 735, and 745 each include multiple diodes connected serially based at least upon voltage ratings of the serially connected diodes.

In this embodiment, diodes 715, 725, 735, and 745 are connected so as to conduct current from the positive terminal of output port Vout toward pulse generator circuits 710, 720, 730, and 740, as pulse generator circuits 710, 720, 730, and 740 in this embodiment are configured to generate negative pulses. In alternative embodiments, where pulse generator circuits are configured to generate positive pulses, diodes may be similarly connected so as to conduct current from the pulse generator circuits to the positive terminal of the output port.

Figure 8:
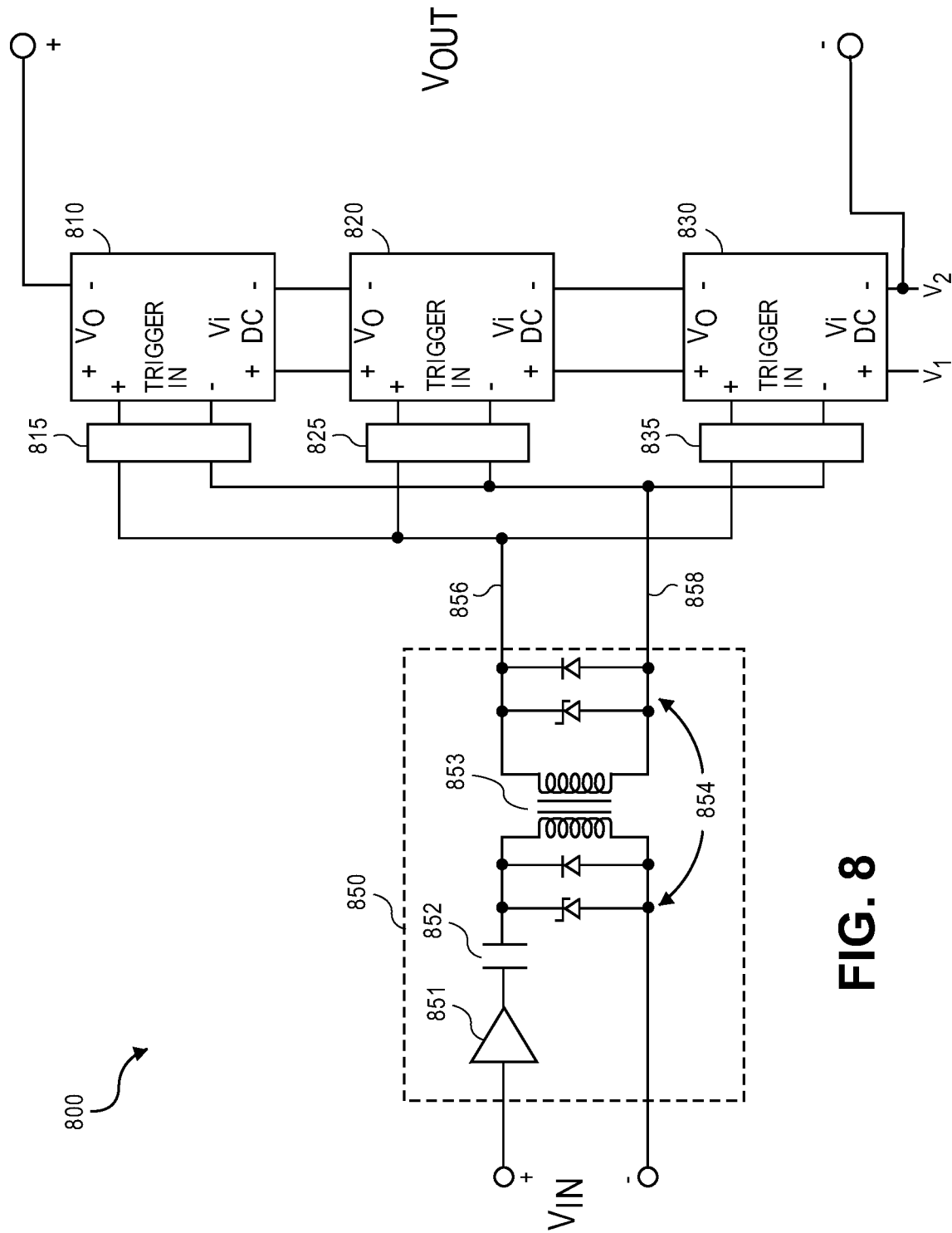
FIG. 8 is an electrical schematic of one of the pulse generator circuits shown in FIG. 7.

FIG. 8 illustrates a pulse generator circuit 800 which may be used for pulse generator circuits 710, 720, 730, and 740 of pulse generator circuit 700 of FIG. 7.

Pulse generator circuit 800 receives input pulses across input port Vin, and generates output pulses across output port Vout in response to the received input pulses.

Pulse generator circuit 800 includes multiple pulse generator stages 810, 820, and 830. In this embodiment, pulse generator circuit 800 also includes driver 850, and optional common mode chokes 815, 825, and 835.

Each of the pulse generator stages 810, 820, and 830 may have characteristics similar to other pulse generator stages discussed herein. For example, each the pulse generator stages 810, 820, and 830 may have characteristics similar to stages 510, 520, and 530 of pulse generator circuit 500 discussed above with reference to FIGS. 5, 6A, and 6B. In some embodiments, fewer or more pulse generator stages may be used.

Each of pulse generator stages 810, 820, and 830 has positive and negative trigger input terminals, power positive and negative DC input terminals, and positive and negative Vo output terminals, and is configured to generate output voltage pulses across the positive and negative Vo output terminals in response to driving signal pulses applied across the positive and negative trigger input terminals. The output voltage pulses are also based on power voltages V1 and V2 respectively received at power positive and negative DC input terminals.

In this embodiment, the negative Vi input terminal of pulse generator stage 830 is connected with the negative terminal of the output port Vout of pulse generator circuit 800. In addition, in this embodiment, the negative Vo output terminal of pulse generator stage 810 is connected with the positive terminal of the output port Vout of pulse generator circuit 800.

In addition, as shown, the positive Vo output terminal of pulse generator 830 is connected with the positive Vi input terminal of pulse generator 820, and the negative Vo output terminal of pulse generator 830 is connected with the negative Vi input terminal of pulse generator 820. Furthermore, the positive Vo output terminal of pulse generator 820 is connected with the positive Vi input terminal of pulse generator 810, and the negative Vo output terminal of pulse generator 820 is connected with the negative Vi input terminal of pulse generator 810.

The driving signal pulses for pulse generator stages 810, 820, and 830 are generated across conductors 856 and 858 by driver 850, which includes amplifier circuit 851, capacitor 852, and transformer 853. In some embodiments, driver 850 also includes clamp circuits 854.

Driver 850 receives an input signal pulse at input port Vin. Driver 850 generates a driving signal pulse across conductors 856 and 858 in response to the input signal pulse. Amplifier circuit 851 receives the input signal pulse, and drives transformer 853 through capacitor 852, which reduces or blocks low frequency and DC signals. In response to being driven by amplifier circuit 851, transformer 853 generates an output voltage pulse across conductors 856 and 858, such that the duration of the output voltage pulse is equal to or substantially equal (e.g. within 10% or 1%) to the duration of the input signal pulse at input port Vin.

In some embodiments, clamp circuits 854 are included at least to dampen potential signals, which may otherwise be caused by resonance. Clamp circuits 854 include parallel diodes, which provide a short-circuit path for any current reversal, and also clamp the maximum voltage across the components connected to the clamp circuits 854.

In some embodiments, transformer 853 has a 1:1 turns ratio. In alternative embodiments, a different turns ratio is used.

Each of pulse generator stages 810, 820, and 830 receives the voltage pulses from driver 850 through a corresponding choke 815, 825, or 835, which blocks high frequency signals, for example, from coupling from the high voltage pulse generator stages 810, 820, and 830. The voltage pulses are received at the positive and negative trigger input terminals and the pulse generator stages 810, 820, and 830 each generate corresponding voltage pulses across the positive and negative Vo output terminals in response to the received voltage pulses from driver 850. The voltage pulses generated across the positive and negative Vo output terminals have durations which are equal to or substantially equal (e.g. within 10% or 1%) to the durations of the voltage pulses received from driver 850.

Figure 9:
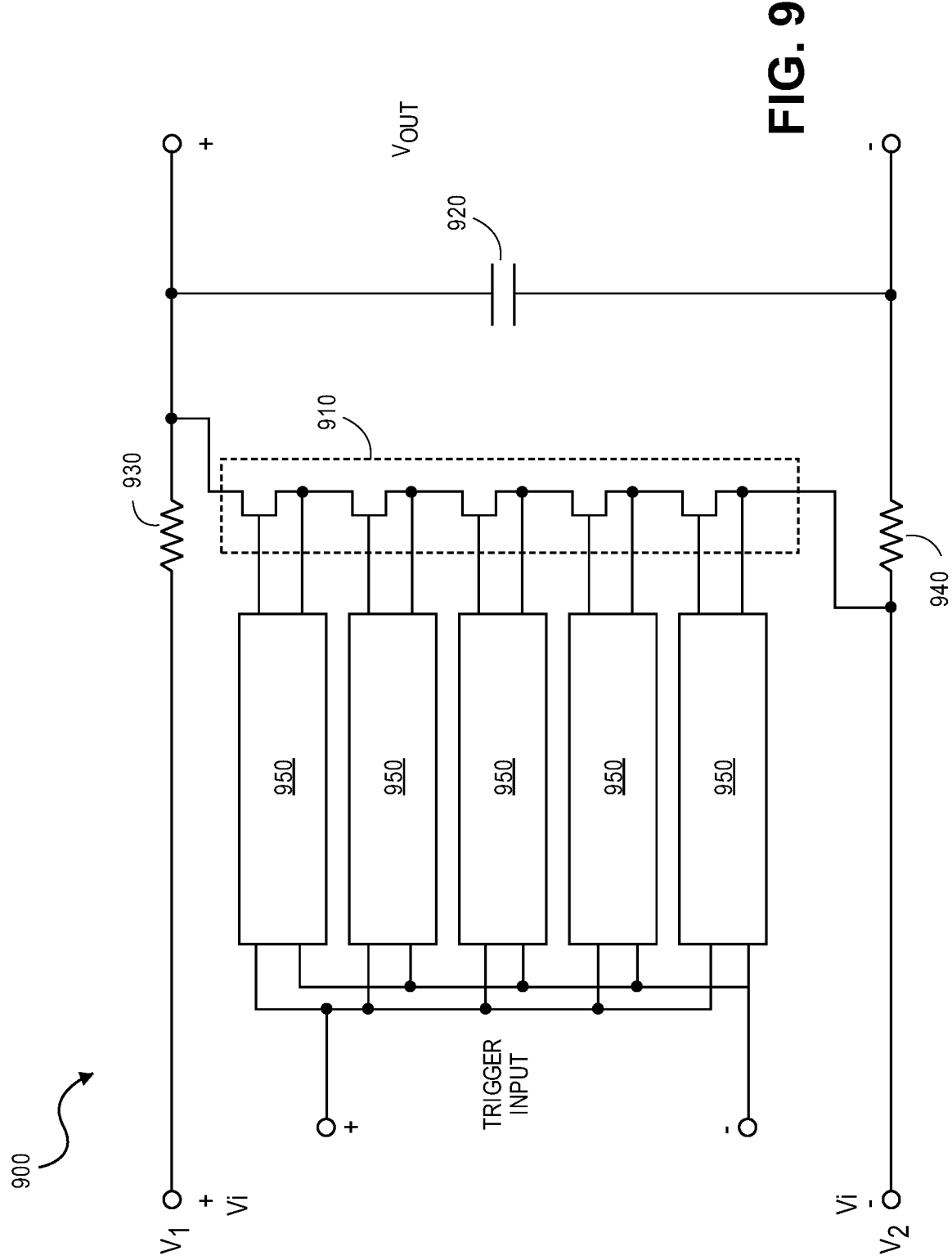
FIG. 9 is an electrical schematic of one of the pulse generator stages shown in FIG. 8.

FIG. 9 illustrates a pulse generator stage 900 which may be used as one of the pulse generator stages 810, 820, and 830 of pulse generator circuit 800 shown in FIG. 8.

Pulse generator stage 900 receives trigger pulses across input port trigger input, and generates output voltages at output port Vout in response to the received trigger pulses. The output voltages are also generated based on power voltages received at power input terminals V1 and V2. Pulse generator stage 900 includes multiple switch drivers 950. Pulse generator stage 900 also includes switch stack 910, capacitor 920, and resistors 930 and 940.

Switch drivers 950 are configured to receive the trigger pulses, and to generate control signals for the switches of switch stack 910 in response to the received trigger pulses, as discussed in further detail below. Each of the control signals is referenced to a voltage specific to the switch being driven. Accordingly, a first switch receives a control signal pulse between first and second voltages, and a second switch receives a control signal pulse between third and fourth voltages, where each of the first, second, third, and fourth voltages are different. In some embodiments, the difference between the first and second voltages is substantially the same as the difference between the third and fourth voltages.

Switch stack 910, capacitor 920, and resistors 930 and 940 cooperatively function with corresponding elements in the other pulse generator stages of pulse generator circuit 800, discussed above with reference to FIG. 8, to generate the voltage pulses across the positive and negative Vo output terminals of pulse generator circuit 800. These elements may, for example, cooperatively function as the corresponding elements discussed above with reference to pulse generator circuit 500 shown in FIGS. 5, 6A, and 6B. For example, these elements may cooperate to generate the voltage pulses across the positive and negative Vo output terminals of pulse generator circuit 800 in response to the power voltages applied to power input terminals V1 and V2 and to the control signals applied to the switches of switch stack 910.

Because the control signals are generated in response to the input pulses received across input port Vin of pulse generator circuit 700 illustrated in FIG. 7 through multiple stages of driving, the control signals cause all of the switches of the switch stacks of pulse generator circuit 700 to be turned on and to be turned off substantially simultaneously. For example, a 15V input pulse having a duration of, for example 100 ns, received at input port Vin of pulse generator circuit 700 may cause the pulse generator circuit 700 to generate a high-voltage (e.g. ~15 kV) output pulse having a duration of about 100 ns. Similarly, a 15V input pulse having a duration of, for example 5 μs, received at input port Vin of pulse generator circuit 700 may cause the pulse generator circuit 700 to generate a high-voltage (e.g. ~15 kV) output pulse having a duration of about 5 μs. Accordingly, the duration of the high-voltage output pulse is substantially the same as a selected duration of an input pulse.

Figure 10:
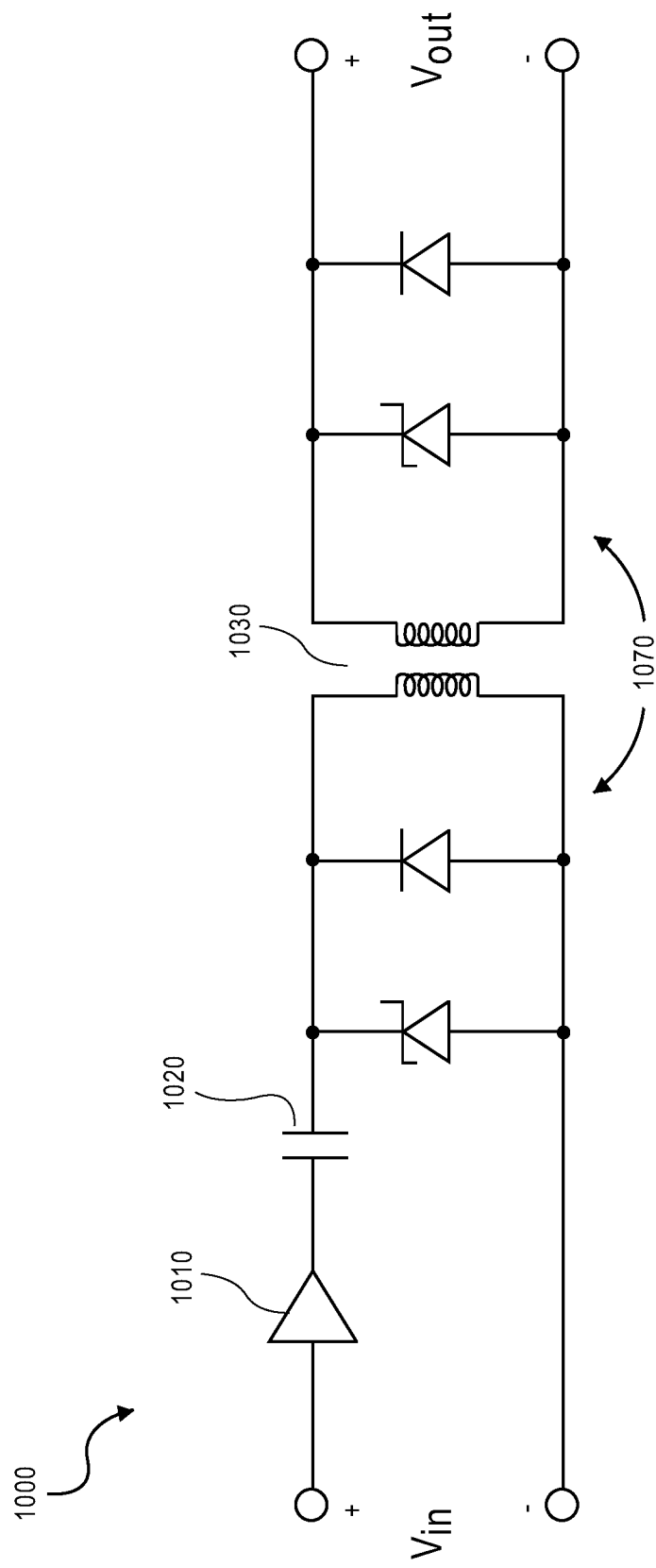
FIG. 10 is an electrical schematic of one of the switch drivers shown in FIG. 9.

FIG. 10 illustrates a switch driver 1000 which may be used as one of the switch drivers shown in FIG. 9.

Switch driver 1000 receives trigger pulses across input port Vin, and generates control signal pulses at output port Vout in response to the received trigger pulses. Switch driver 1000 includes amplifier circuit 1010, capacitor 1020, and transformer 1030. In some embodiments, switch driver 1000 also includes clamps circuits 1070.

Amplifier circuit 1010 receives the trigger pulses, and drives transformer 1030 through capacitor 1020, which reduces or blocks low frequency and DC signals. In response to being driven by amplifier circuit 1010, transformer 1030 generates control signal pulses at output port Vout, such that the duration of the control signal pulses is equal to or substantially equal (e.g. within 10% or 1%) to the duration of the trigger pulses at input port Vin.

In some embodiments, amplifier circuit 1010 includes multiple amplifier integrated circuits. For example, for increased current driving capability, multiple amplifier integrated circuits may be connected in parallel to form amplifier circuit 1010. For example, 2, 3, 4, 5, 6, 7, 8 or another number of amplifier integrated circuits may be used.

In some embodiments, clamp circuits 1070 are included at least to dampen potential signals, which may otherwise be caused by resonance. Clamp circuits 1070 include parallel diodes, which provide a short-circuit path for any current reversal, and also clamp the maximum voltage across the components connected to the clamp circuits 1070.

In some embodiments, the drivers 750, 850, and 1000 receive power from a DC-DC power module which is isolated from the power supply for the Marx generator. This ensures the cutoff of ground coupling.

In some embodiments, transformer 1030 has a 1:1 turns ratio. In alternative embodiments, a different turns ratio is used.

In some embodiments, in order to obtain very fast switching, the transformers 1030 has fewer than 5 turns in the primary winding and fewer than 5 turns in the secondary winding. For example, in some embodiments, the transformer 1030 has 1, 2, 3, or 4 turns in each of the primary and secondary windings. In some embodiments, the transformer 1030 has less than a complete turn, for example, ½ turn in the primary and secondary windings. The low number of turns in each of the primary and secondary windings allows for a low inductance loop and increases the current risetime in the secondary winding, which charges the input capacitance of the MOSFET switches.

Transformers for triggering MOSFETs in conventional applications require high coupling, high permeability, and a low-loss core in order to ensure current transfer efficiency. From pulse to pulse, the residual flux in the core needs to be cleared in order to avoid saturation when the transformer is operated at high frequency. Conventionally, a resetting circuit, which involves a third winding, to dissipate the core energy is used.

In some embodiments, lossy transformers, such as that typically used as an electromagnetic interference (EMI) choke to confine high frequency signals and dissipate their energy as heat are used to trigger the switches. For example, the transformers may have a voltage time constant less than 100V μs. In some embodiments, the Transformers have a voltage time constant less than 50V μs, 30V μs, 20V μs, 10V μs, or 5V μs. The use of the lossy transformer is contrary to the common practice in power electronics.

Although the high frequency flux is dampened due to the loss of the core (eddy loss, hysteresis loss, and resistive loss), the lossy transformers still allow sufficient confinement of the magnetic flux and provides sufficient coupling. In addition, the flux also decreases quickly in response to the signal on the primary winding being removed. The flux decay process usually takes approximately several microseconds.

Having such a transformer conventionally seems disadvantageous, but for coupling nanosecond to a few microsecond pulses, such a transformer is preferably used. Consequently, the following benefits are achieved: 1) high voltage, high frequency transient coupling from the high-voltage Marx generators to the low-voltage drivers is suppressed; 2) because of the loss in the transformer cores, the residual flux from previous pulses are dissipated faster than common low-loss transformer cores, such that the resetting winding is not needed and is not present.

A benefit of the switch driver 1000 is that it limits the output pulse duration. Because the switch control signals are generated by transformer 1030, even if circuitry generating the input trigger signals at input port Vin were to generate a pulse of indefinite length, the transformer would saturate, causing the control signals to turn off the switches.

Figure 11:
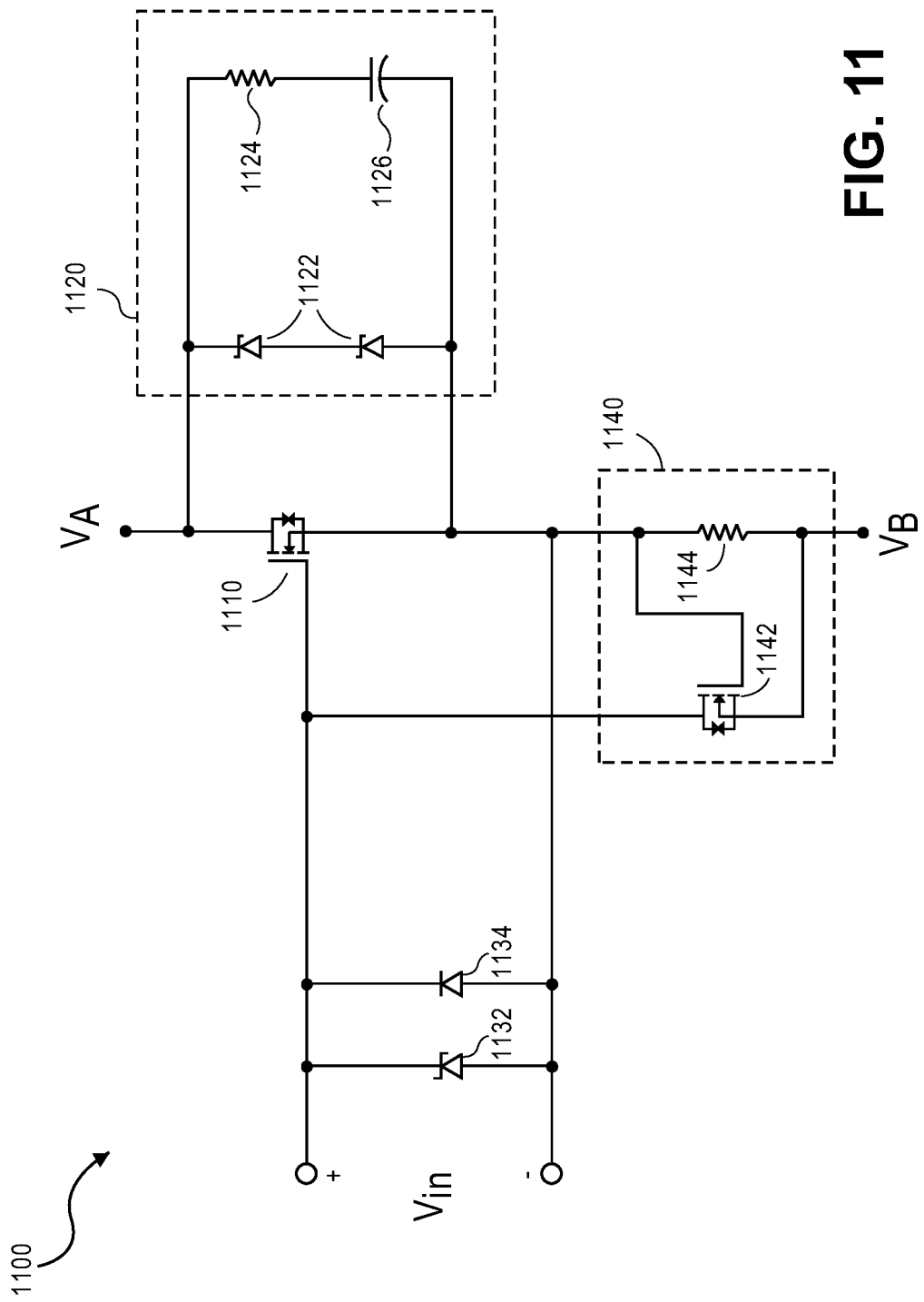
FIG. 11 is an electrical schematic of an alternative switch element.

FIG. 11 illustrates an example of a switch element 1100 comprising components which may be used in the switch stacks discussed here. Switch element 1100 includes switch 1110, and selectively forms a conductive or low resistance path between terminals VA and VB in response to a control voltage applied to input port Vin.

In some embodiments, switch 1110 is a transistor, such as a MOSFET. In some embodiments, switch 1110 is another type of switch. In some embodiments, switch 1110 has a turn on time of less than 5 ns, about 5 ns, about 10 ns, about 25 ns, about 15 ns, about 75 ns, about 100 ns, or greater than 100 ns.

In some embodiments, switch element 1100 also includes snubber circuit 1120. In some embodiments, the turn on times of the switches of the switch stacks are not identical. In order to prevent voltages greater than that which switch 1110 can tolerate, snubber circuit 1120 provides a current shunt path bypassing switch 1110. Diodes 1122 provide a low-frequency current path, and the combination of the capacitor 1126 and resistor 1124 provide a high-frequency current path.

In some embodiments, switch element 1100 also includes optional overcurrent protection circuit 1140. Overcurrent protection circuit 1140 includes switch 1142 and sense resistor 1144.

Current flowing from terminal VA to terminal VB is conducted through sense resistor 1144. Accordingly, a voltage is generated across sense resistor 1144 when the current flows from terminal VA to terminal VB. The generated voltage controls a conductive state of switch 1142. If the current flowing from terminal VA to terminal VB is greater than a threshold, the generated voltage causes the switch 1142 to conduct. As a result, switch 1142 reduces the control voltage of switch 1110. In response to the reduced control voltage, switch 1110 becomes less conductive or turns off. Consequently, the current which may be conducted from terminal VA to terminal VB is limited by overcurrent protection circuit 1140.

In some embodiments, a current limiting resistor is placed between the gate of switch 1110 and the drain of switch 1142 to prevent switch 1142 from experiencing current greater than that which would cause damage.

In the embodiments discussed herein, MOSFET switches are used. In alternative embodiments, other switches are used. For example, in some embodiments, thyristors, IGBTs or other semiconductor switches are used.

Figure 12:
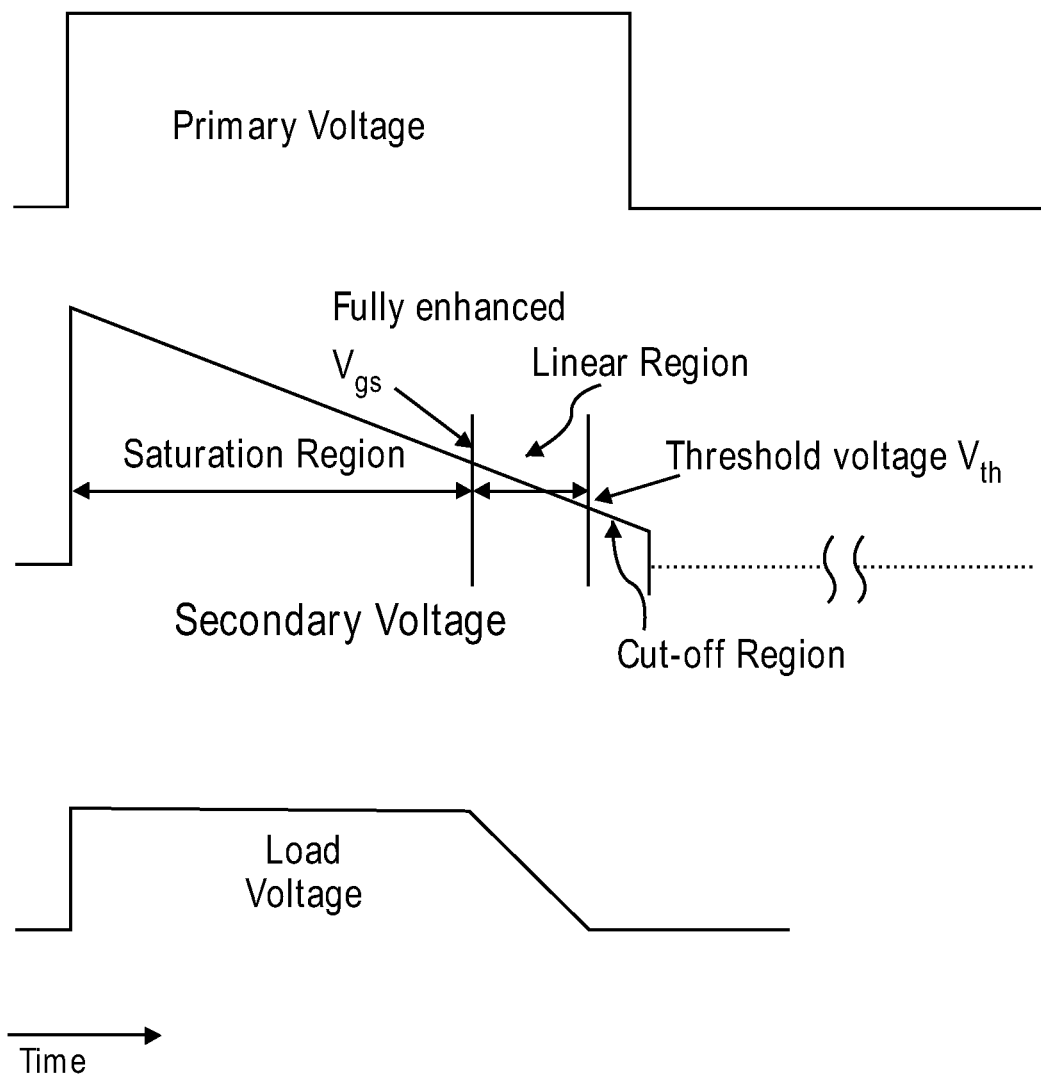
FIG. 12 is a waveform diagram illustrating the operation of a transformer and a control voltage to a MOSFET gate.

An example of the operation of the transformer is illustrated in FIG. 12. The voltage at the input primary inductor is substantially a square waveform, but the voltage at the secondary inductor, which is the MOSFET's gate-source voltage, tapers as the voltage magnitude decreases toward zero, for example, within a period of several microseconds. After a reduction in voltage at the secondary inductor due to transformer saturation, the switch receiving the voltage enters a linear region of operation from a saturation region of operation when the voltage is lower than the fully enhanced Vgs. As a result, the resistance of the switch increases and the output voltage across the load also shows a tapered profile. When the voltage at the secondary inductor decreases to a value less than the turn-on threshold of a MOSFET (Vth), the MOSFET will be shut off. Once the MOSFET is off, even if the duration of the trigger signal is extended, the switch no longer conducts and can be considered an open circuit. The waveform of the voltage at the secondary inductor therefore limits the duration of high voltage output pulses from each panel, for example, to be several microseconds or less.

In some embodiments, the duration of the trigger signal is short enough that the switches remain in saturation because the reduction in voltage at the secondary inductor is insufficient to cause the switches to enter linear region operation. In such embodiments, the load voltage pulses do not exhibit the tapering illustrated in FIG. 12. For example, in such embodiments the load voltage pulses may be substantially square.

In some embodiments, the switch stacks discussed herein include switches, as discussed above, as well as other components.

In some embodiments, when generating pulses of a duration less than a threshold, the shape of the pulses are substantially square. In some embodiments, when generating pulses of the duration greater than a threshold, the shape of the pulses are substantially square for a duration substantially equal (e.g. within 10% or 1%) to the threshold. During the time after the threshold, the voltage of such long pulses drops toward 0 V. In some embodiments, the drop toward 0 V is substantially linear. In some embodiments, the drop toward 0 V is substantially exponential.

Figure 13:
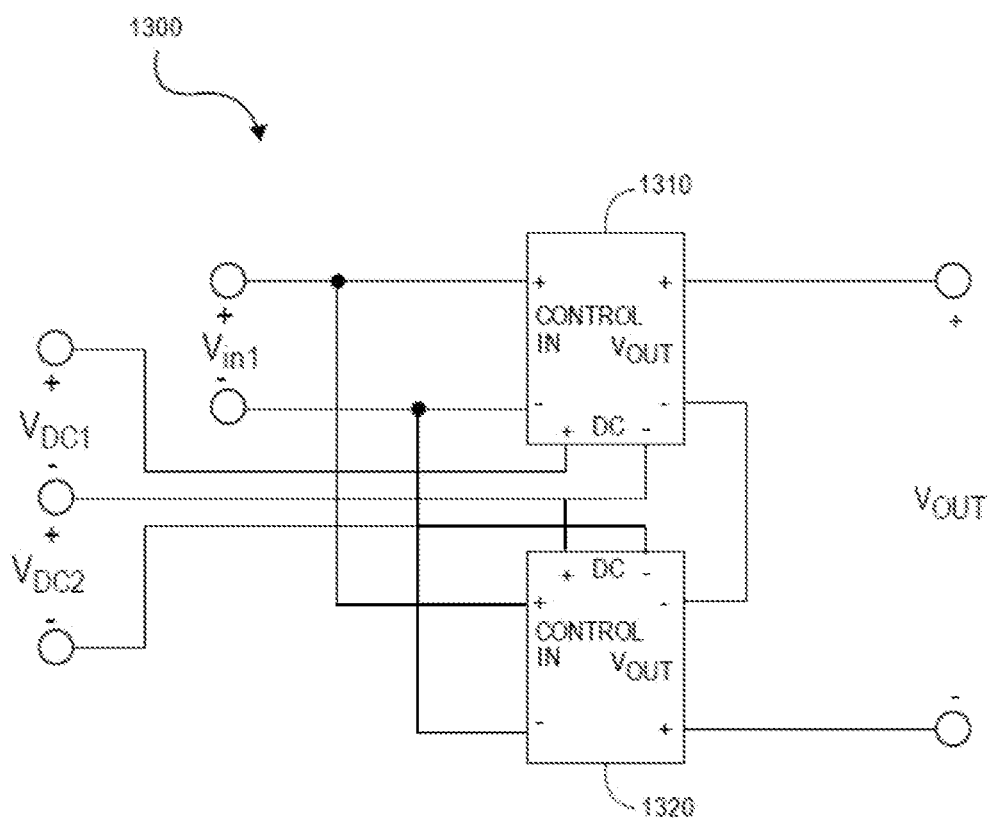
FIG. 13 is an alternative electrical schematic of a pulse generator shown in FIG. 1.

FIG. 13 illustrates an alternative pulse generator circuit 1300 which may be used inside nsPEF system 100 of FIG. 1.

Pulse generator circuit 1300 receives input pulses across input port Vin and DC voltages at input ports VDC1 and VDC2, and generates output pulses across output port Vout in response to the received input pulses and DC voltages.

Pulse generator circuit 1300 includes multiple pulse generator circuits 1310 and 1320. In this embodiment, two pulse generator circuits are used. In alternative embodiments, more pulse generator circuits are used. For example, in some embodiments, 3, 4, 5, 10 or another number of pulse generator circuits having their output ports serially connected, as discussed below with reference to pulse generator circuit 1300, are used.

Each of pulse generator circuits 1310 and 1320 may be similar to the other pulse generator circuits discussed herein. For example pulse generator circuits 1310 and 1320 may be similar to or may be substantially identical to pulse generator circuit 700 discussed above with reference to FIG. 7.

Each of pulse generator circuits 1310 and 1320 receive the same input pulse signal across their respective Control In input ports. In response, each of pulse generator circuits 1310 and 1320 generate high voltage pulses across their respective Vout output ports. Because the Vout output ports of pulse generator circuits 1310 1320 are serially connected, the voltage pulse generated by pulse generator circuits 1310 and 1320 across output port Vout of pulse generator circuit 1300 is substantially equal (e.g. within 10% or 1%) to the sum of the voltages of the pulses respectively generated by pulse generator circuits 1310 and 1320.

Figure 14:
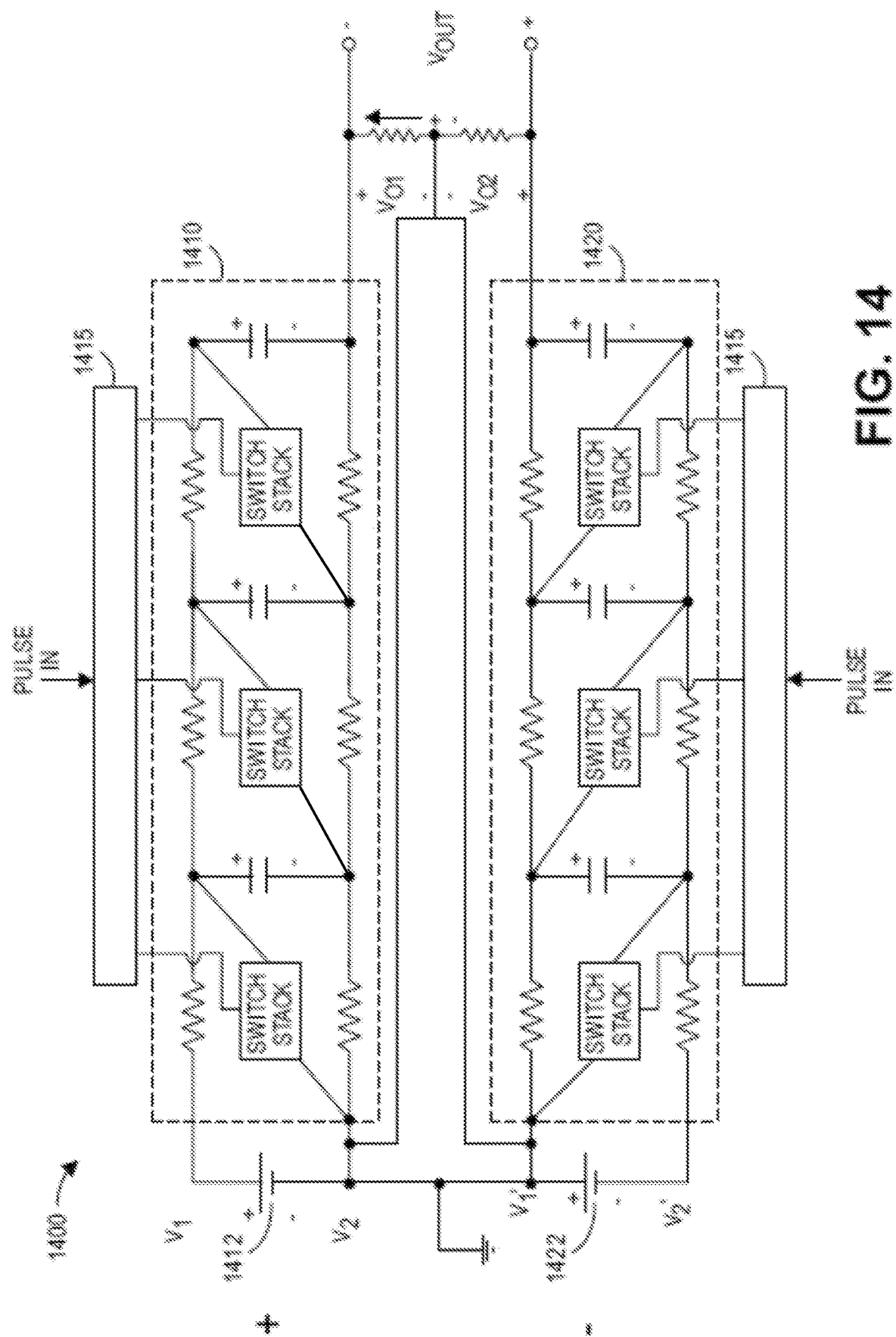
FIG. 14 is an alternative electrical schematic of a pulse generator shown in FIG. 1.

FIG. 14 illustrates an alternative pulse generator circuit 1400 which may be used inside nsPEF system 100 of FIG. 1, and which has characteristics similar to the pulse generator 1300 of FIG. 13. Pulse generator circuit 1400 includes pulse generators 1410 and 1420, drivers 1415 and 1425, and power supplies 1412 and 1422.

Pulse generator circuit 1400 includes multiple pulse generator circuits 1410 and 1420. In this embodiment, two pulse generator circuits are used. In alternative embodiments, more pulse generator circuits are used. Each of pulse generator circuits 1410 and 1420 may be similar to the other pulse generator circuits discussed herein.

Pulse generator circuit 1400 receives input pulses at each of drivers 1415 and 1425, which may be similar to driver 850 discussed above with reference to FIG. 8. Pulse generator circuit 1400 generates output pulses across output port Vout in response to the received input pulses. The output voltage pulses are also based on power voltages received from power supplies 1412 and 1422.

Each of drivers 1415 and 1425 receive an input pulse signal. In response to the received input signals, drivers 1415 and 1425 respectively generate driving signal pulses for pulse generator circuits 1410 and 1420. In response to the driving signal pulses, each of pulse generator circuits 1410 and 1420 generate high voltage pulses across their respective output ports Vo1 and Vo2. Because the Vo1 and Vo2 output ports of pulse generator circuits 1410 and 1420 are serially connected, the voltage pulse generated by pulse generator circuits 1410 and 1420 across output port Vout of pulse generator circuit 1400 is substantially equal (e.g. within 10% or 1%) to the sum of the voltages of the pulses respectively generated by pulse generator circuits 1410 and 1420.

In this embodiment, pulse generator circuit 1410 generates a high voltage pulse across its output port Vo1 which is substantially equal (e.g. within 10% or 1%) to three times the voltage of power supply 1412, $(-3 \times [V1-V2])$. In addition, pulse generator circuit 1420 generates a high voltage pulse across its output port Vo2 which is substantially equal (e.g. within 10% or 1%) to three times the voltage of power supply 1414 $(3 \times [V'1-V'2])$. As a result, pulse generator circuit 1400 generates a voltage of $(3 \times [V'1-V'2])-(-3 \times [V1-V2])$ across its output port Vout.

In some embodiments, a single driver circuit connected to both pulse generator circuit 1410 and 1420 is used instead of drivers 1415 and 1425. In such embodiments, the single driver circuit generates driving signal pulses for both pulse generator circuits 1410 and 1420 in response to an input pulse signal.

Figure 15:
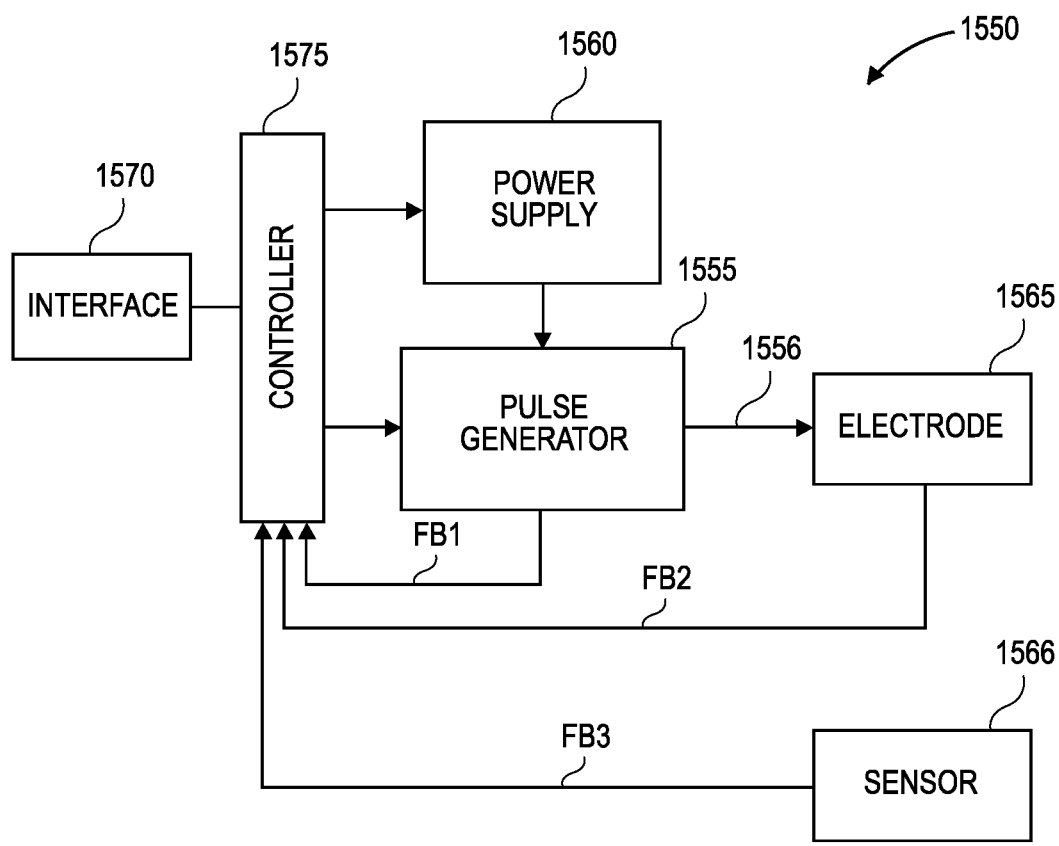
FIG. 15 is a block diagram of a nsPEF treatment system.

FIG. 15 is a block diagram of a nsPEF treatment system 1550, which has characteristics similar to or identical to those of nsPEF system 100 illustrated in FIG. 1. NsPEF treatment system 1550 includes pulse generator 1555, power supply 1560, electrode 1565, interface 1570, and controller 1575.

Pulse generator 1555 may be similar or identical to any of the pulse generator circuits discussed herein. For example, pulse generator 1555 may be configured to generate pulses having a voltage magnitude corresponding with power voltages received from power supply 1560 and having pulse widths and other characteristics corresponding with control signals received from controller 1575. In alternative embodiments, other pulse generator circuits may be used.

Electrode 1565 may be similar or identical to any of the electrodes discussed herein. For example, electrode 1565 may be similar or identical to electrodes 300 and 400 discussed above with reference to FIGS. 3 and 4. Electrode 1565 is configured to receive nsPEF pulses generated by pulse generator 1555 from conductor 1556 and is configured to deliver nsPEF pulses to a patient undergoing therapeutic nsPEF treatment. In alternative embodiments, other therapeutic electrodes may be used.

Sensor 1566 may include one or more of a thermocouple, a voltage probe, a current probe, an impedance probe, a capacitance probe, a light sensor, a humidity sensor, a tissue monitoring probe, and a chemical analysis probe. Sensor 1566 may be configured to sense one or more characteristics of the patient, the electrode 1565, the nsPEF pulses delivered by the electrode 1565, and effects of the nsPEF pulses delivered by the electrode 1565.

Power supply 1560 is configured to provide power voltages to pulse generator 1555. For example, in embodiments where pulse generator 1555 is similar to pulse generator circuit 700 illustrated in FIG. 7, power supply 1560 may be configured to provide power voltages corresponding with power voltages V1 and V2 of pulse generator circuit 700. In some embodiments, power supply 1560 generates and provides power voltages which have a voltage level corresponding with a control signal from controller 1575.

Interface 1570 is configured to receive input from a user identifying various parameters and characteristics of the nsPEF pulses to be applied to the patient. For example, interface 1570 may be configured to receive input identifying or specifying values for one or more characteristics of one or more nsPEF pulses to be applied to the patient. For example, the characteristics may include one or more of an amplitude, a polarity, a width, a rise time, and a fall time of one or more nsPEF pulses to be applied to the patient. Additionally or alternatively, the characteristics may include one or more of a frequency and a pulse quantity of a sequence of nsPEF pulses to be applied to the patient. Furthermore, the characteristics may additionally or alternatively include a result of the nsPEF pulses to be applied to the patient, such as a maximum temperature for the treated tissue of the patient. Other characteristics may additionally or alternatively be identified or specified by the received input.

In addition, interface 1570 is configured to communicate the characteristics identified or specified by the received input to controller 1575.

Controller 1575 is configured to generate and provide one or more control signals to pulse generator 1555 and to power supply 1560 based at least partly on the communicated characteristics received from interface 1570. Additionally, pulse generator 1555, power supply 1560, and electrode 1565 are collectively configured to, in response to the control signals from controller 1575, generate nsPEF pulses having characteristics corresponding with the control signals.

In this embodiment, one or more of pulse generator 1555, electrode 1565, and sensor 1566 are configured to generate corresponding feedback signals FB1, FB2, and FB3 representing measured parametric characteristics of the nsPEF pulses applied to the patient or other signals of nsPEF treatment system 1550. In some embodiments, the parametric characteristics of the nsPEF pulses represented by the feedback signals FB1, FB2, and FB3 include one or more of an amplitude, a polarity, a width, a rise time, and a fall time of the nsPEF pulses. In some embodiments, the parametric characteristics of the nsPEF pulses represented by the feedback signals, FB2, and FB3 additionally or alternatively include one or more of current and voltage applied to the tissue so that one or more of tissue impedance, tissue inductance, tissue capacitance, instantaneous power applied to the tissue, and energy applied to the tissue may be calculated. In some embodiments, the parametric characteristics represented by the feedback signal FB1 may additionally or alternatively include one or more of a voltage at a capacitor being charged during a charge mode of pulse generator 1555, voltage and/or current characteristics of a control signal of pulse generator 1555, voltage and/or current characteristics of a power supply signal of pulse generator 1555, voltage and/or current characteristics of a pulse generated by pulse generator 1555, and voltage and/or current characteristics of another input, output, or internal signal of pulse generator 1555. Additionally or alternatively, the parametric characteristics may include a frequency of a sequence of nsPEF pulses. Furthermore, the parametric characteristics may additionally or alternatively include a temperature of the treated tissue of the patient. The feedback signals, FB2, and FB3 may correspond or represent other measured parametric characteristics of one or more of the nsPEF pulses applied to the patient, the patient, the environment, and the nsPEF treatment system 1550.

In some embodiments, controller 1575, power supply 1560, pulse generator 1555, electrode 1565, and optionally sensor 1566 collectively form a feedback loop which causes one or more parametric characteristics of the nsPEF pulses applied to the patient to have measured values substantially equal (e.g. within 10% or 1%) to the values of corresponding characteristics identified in the input received by interface 1570.

For example, interface 1570 may receive input specifying a value of 15 kV for an amplitude of the nsPEF pulses applied to the patient. In addition, the controller 1575 may be configured to, in response to a feedback signal FB2 from electrode 1565, a feedback signal FB1 from pulse generator 1555, or a feedback signal FB3 from sensor 1566 indicating that the measured amplitude of the nsPEF pulses applied to the patient is less than (or greater than) 15 kV, change a control signal provided to power supply 1560. In response to the changed control signal, power supply 1560 may be configured to increase (or decrease) the voltage of power signals provided to pulse generator 1555 such that the amplitude of the nsPEF pulses generated and applied to the patient increases (or decreases) to or toward 15 kV.

Similarly, interface 1570 may receive input specifying a value of 150 ns for a pulse width of the nsPEF pulses applied to the patient. The controller 1575 may be configured to, in response to a feedback signal FB3 from sensor 1566, a feedback signal FB2 from electrode 1565, or a feedback signal FB1 from pulse generator 1555 indicating that the measured pulse width of the nsPEF pulses applied to the patient is greater than (or less than) 150 ns, change a control signal provided to pulse generator 1555. In response to the changed control signal, pulse generator 1555 may be configured to generate and apply to the patient nsPEF pulses having decreased (or increased) pulse width. As a result, one or more of the feedback signals FB1, FB2, and FB3 causes the controller 1575 to generate control signals which cause the pulse generator 1555 to generate and apply nsPEF pulses having pulse widths decreased (or increased) to or toward 150 ns.

In some embodiments, the feedback loop is controlled using a Proportional-Integral-Derivative (PID) method. For example, using the PID method, controller 1575 may be configured to continuously or substantially continuously calculate an error value as the difference between a desired value perceived at interface 1570 and a corresponding measured parameter. In addition, using the PID method, controller 1575 may be configured to continuously or substantially continuously calculate the control signals as a sum of one or more of: a first constant times the error signal, a second constant times an integral of the error signal, and a third constant times a derivative of the error signal, where the first, second, and third constants may be positive, negative, or equal to zero. Other custom or standard control methods may additionally or alternatively be used.

In some embodiments, the feedback loop is controlled using a lookup table to determine a next value based on a measured value. In some embodiments, the feedback loop is controlled by reducing or increasing a value by a fixed amount or step size based on a determination of whether a measured value is greater than or less than a threshold.

Figure 16:
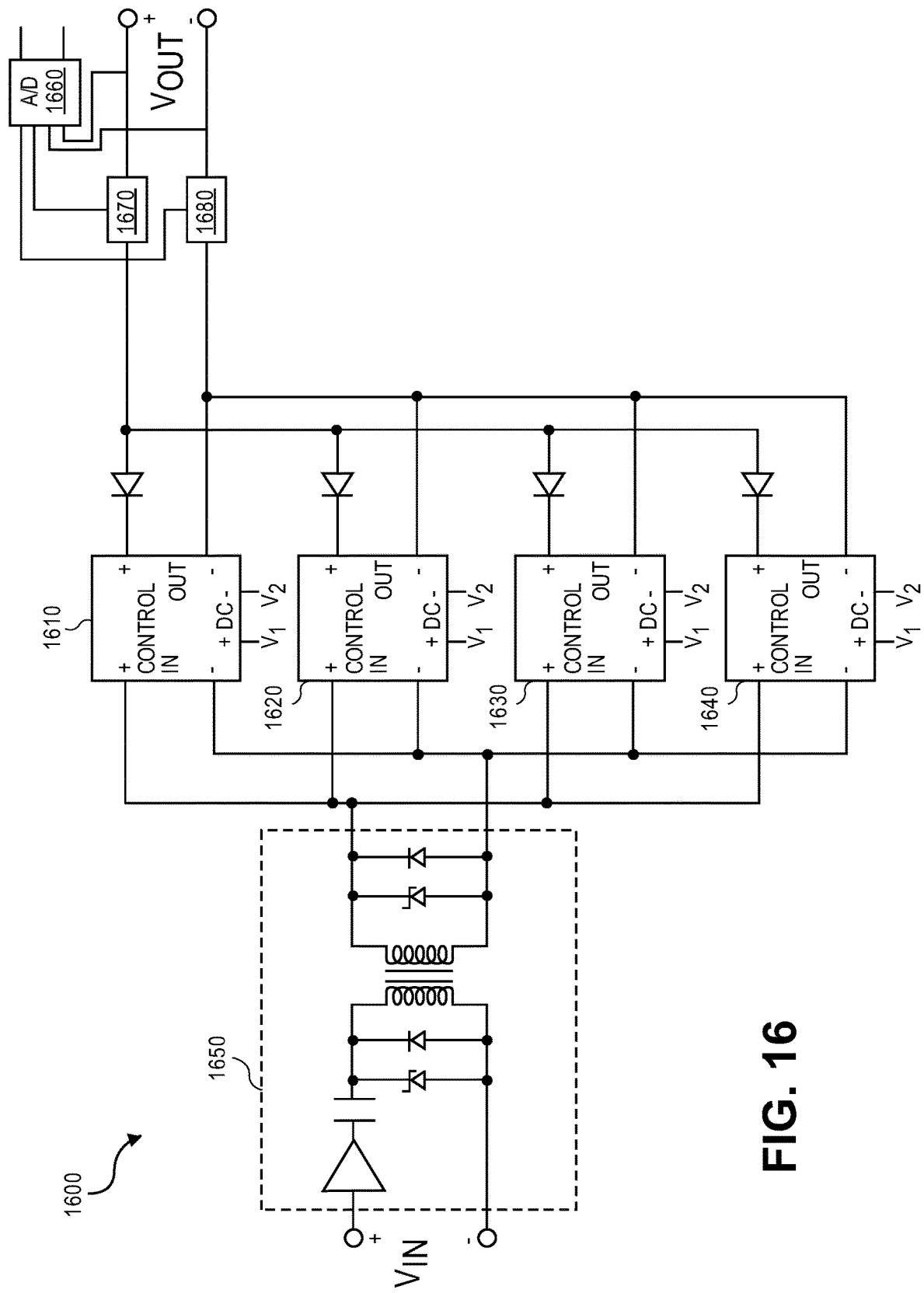
FIG. 16 is a schematic illustration of an alternative pulse generator.

FIG. 16 illustrates an alternative pulse generator 1600 which may be used as pulse generator 1555 of nsPEF treatment system 1550 illustrated in FIG. 15. Pulse generator 1600 may have features similar to or identical to other pulse generator circuits discussed herein. For example, pulse generator circuit 1600 may have features similar to or identical to pulse generator circuit 700 of FIG. 7.

For example, pulse generator 1600 includes the driver circuit 1650 which may be similar to or identical to driver 750 of pulse generator circuit 700. In addition, pulse generator 1600 includes pulse generator circuits 1610, 1620, 1630, and 1640, which may respectively be similar or identical to pulse generator circuits 710, 720, 730, and 740.

Pulse generator 1600 also includes, or in some embodiments is connected to, analog-to-digital converter 1660. Furthermore, pulse generator 1600 additionally or alternatively includes, or in some embodiments is connected to, current monitors 1670 and 1680.

In this embodiment, analog-to-digital (A/D) converter 1660 includes a first channel having inputs which are respectively connected to the positive (+) and negative (−) voltage output terminals of pulse generator 1600. In some embodiments, a first low input impedance differential buffer (not shown) is connected to the positive (+) and negative (−) voltage output terminals of pulse generator 1600, and drives the inputs of analog-to-digital converter 1660. In some embodiments, a probe, such as a Tektronix P6015A Passive High Voltage Probe (not shown) is connected to the positive (+) and negative (−) voltage output terminals of pulse generator 1600, and drives the inputs of analog-to-digital converter 1660.

In some embodiments, only the positive (+) voltage output terminal is connected to analog-to-digital converter 1660. In some embodiments, the positive (+) voltage output terminal is connected to analog-to-digital converter 1660 through a voltage divider. In such embodiments, the voltage at the positive (+) voltage output terminal is ground referenced, and the ground is also connected to analog-to-digital converter 1660. For example, the positive (+) voltage output terminal is ground referenced if the negative (−) voltage output terminal of pulse generator 1600 is at the ground voltage.

In addition, analog-to-digital converter 1660 is configured to generate a first digital output representing the voltage difference between the positive (+) and negative (−) voltage output terminals of pulse generator 1600. When used in the nsPEF treatment system 1550 of FIG. 15, the first digital output may be used as a feedback signal for controller 1575. In some embodiments, analog-to-digital converter 1660 generates the first digital output based on either, but not both, of the voltages at the positive (+) and negative (−) voltage output terminals.

In this embodiment, analog-to-digital converter 1660 also includes a second channel having inputs which are respectively connected to the current monitors 1670 and 1680, and the current monitors 1670 and 1680 are respectively connected to the positive (+) and negative (−) voltage output terminals of pulse generator 1600. In some embodiments, a second low input impedance differential buffer (not shown) is connected to the current monitors 1670 and 1680, and drives the inputs of analog-to-digital converter 1660.

In addition, analog-to-digital converter 1660 is configured to generate a second digital output representing the current difference between the currents flowing through positive (+) and negative (−) voltage output terminals of pulse generator 1600. When used in the nsPEF treatment system 1550 of FIG. 15, the second digital output may be used as a feedback signal for controller 1575. In some embodiments, analog-to-digital converter 1660 generates the second digital output based on either, but not both, of inputs from the current monitors 1670 and 1680.

In some embodiments, current monitors 1670 and 1680 each include a sense resistor and an amplifier. The sense resistor is configured to generate a voltage response of the current flowing therethrough, and the amplifier generates an input for the analog-to-digital converter based on the voltage across the sense resistor.

In some embodiments, current monitors 1670 and 1680 include a current monitor, such as Pearson Current Monitor 2878, which generates a voltage in response to a sensed current.

In some embodiments, pulse generator 1600 generates either, but not both, of the first and second digital outputs. In some embodiments, one or more single channel analog-to-digital converters are used instead of or in addition to analog-to-digital converter 1660.

In some embodiments, only single current monitor is used. The single current monitor may monitor the current of either of the positive (+) and negative (−) voltage output terminals of pulse generator 1600.

Figure 17:
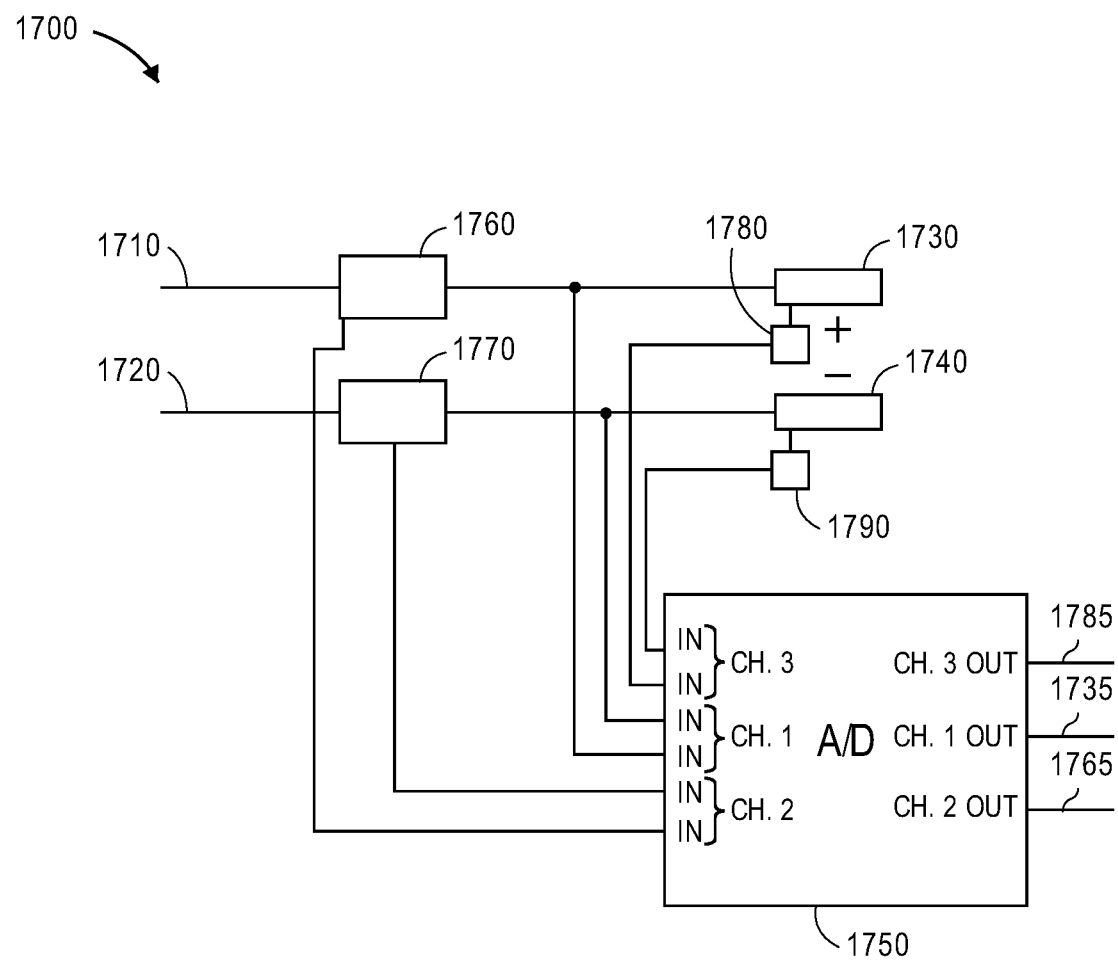
FIG. 17 is a schematic illustration of an electrode which may be used in the nsPEF treatment system of FIG. 15.

FIG. 17 is a schematic illustration of an electrode 1700 which may, for example, be used as electrode 1565 in nsPEF treatment system 1550 of FIG. 15. Electrode 1700 may be similar or identical to any of the electrodes discussed herein. For example, electrode 1700 may be similar or identical to electrodes 300 and 400 discussed above with reference to FIGS. 3 and 4.

Electrode 1700 is configured to receive nsPEF pulses across input terminals 1710 and 1720 and to deliver nsPEF pulses to a patient undergoing therapeutic nsPEF treatment through positive (+) and negative (−) output therapeutic electrodes 1730 and 1740.

Electrode 1700 includes, or in some embodiments is connected to, analog-to-digital converter 1750. Furthermore, electrode 1700 additionally or alternatively includes, or in some embodiments is connected to, current monitors 1760 and 1770. In addition, electrode 1700 includes thermal sensors 1780 and 1790. In some embodiments, electrode 1700 includes either but not both of thermal sensors 1780 and 1790.

In this embodiment, analog-to-digital converter 1750 includes a first channel having inputs which are respectively connected to the positive (+) and negative (−) voltage output therapeutic electrodes 1730 and 1740. In some embodiments, a first low input impedance differential buffer (not shown) is connected to the positive (+) and negative (−) voltage output therapeutic electrodes 1730 and 1740 and drives the inputs of the first channel of analog-to-digital converter 1750. In some embodiments, a probe, such as a Tektronix P6015A Passive High Voltage Probe (not shown) is connected to the positive (+) and negative (−) voltage output therapeutic electrodes 1730 and 1740, and drives the inputs of analog-to-digital converter 1750.

In addition, analog-to-digital converter 1750 is configured to generate a first digital output at output terminal 1735 representing the voltage difference between the positive (+) and negative (−) voltage output therapeutic electrodes 1730 and 1740. When used in the nsPEF treatment system 1550 of FIG. 15, the first digital output may be used as a feedback signal for controller 1575. In some embodiments, analog-to-digital converter 1750 generates the first digital output based on either, but not both, of the voltages at the positive (+) and negative (−) voltage output therapeutic electrodes 1730 and 1740.

In this embodiment, analog-to-digital converter 1750 also includes a second channel having inputs which are respectively connected to the current monitors 1760 and 1770, and the current monitors 1760 and 1770 are respectively connected to the positive (+) and negative (−) voltage output therapeutic electrodes 1730 and 1740. In some embodiments, a second low input impedance differential buffer (not shown) is connected to the current monitors 1760 and 1770 and drives the inputs of the second channel of analog-to-digital converter 1750.

In addition, analog-to-digital converter 1750 is configured to generate a second digital output at output terminal 1765 representing the current difference between the currents flowing through positive (+) and negative (−) voltage output therapeutic electrodes 1730 and 1740. When used in the nsPEF treatment system 1550 of FIG. 15, the second digital output may be used as a feedback signal for controller 1575. In some embodiments, analog-to-digital converter 1750 generates the second digital output based on either, but not both, of inputs from the current monitors 1760 and 1770.

In this embodiment, analog-to-digital converter 1750 also includes a third channel having inputs which are respectively connected to the thermal sensors 1780 and 1790, and the thermal sensors 1780 and 1790 are respectively thermally coupled to the positive (+) and negative (−) voltage output therapeutic electrodes 1730 and 1740.

In some embodiments, a third low input impedance differential buffer (not shown) is connected to the thermal sensors 1780 and 1790, and drives the inputs of the third channel of analog-to-digital converter 1750.

Analog-to-digital converter 1750 may be configured to generate a third digital output at output terminal 1785 representing a temperature of at least one of positive (+) and negative (−) voltage output therapeutic electrodes 1730 and 1740. When used in the nsPEF treatment system 1550 of FIG. 15, the third digital output may be used as a feedback signal for controller 1575. In some embodiments, analog-to-digital converter 1750 generates the third digital output based on either, but not both, of inputs from the thermal sensors 1780 and 1790.

In some embodiments, the thermal sensors 1780 and 1790 are not coupled to the positive (+) and negative (−) voltage output therapeutic electrodes 1730 and 1740, but are, instead, coupled to first and second pins which contact the patient. In such embodiments, the first and second pins may contact the patient to sense tissue temperature, and the therapeutic electrodes 1730 and 1740 may contact the patient to deliver nsPEF pulses.

In some embodiments, one or more thermal sensors separate from electrode 1565 contact the patient and have a cable providing thermal information to controller 1575, where at least part of the cable is different from the cable connecting electrode 1565 and controller 1575.

In some embodiments, electrode 1565 includes at least one laser thermometer, such as an IR laser thermometer, which provides thermal information corresponding with that of thermal sensors 1780 and 1790.

In various embodiments, pulse generator 1700 generates any one, two, or all of the first, second, and third digital outputs. In some embodiments, one or more single channel analog-to-digital converters are used instead of or in addition to analog-to-digital converter 1750.

Figure 18:
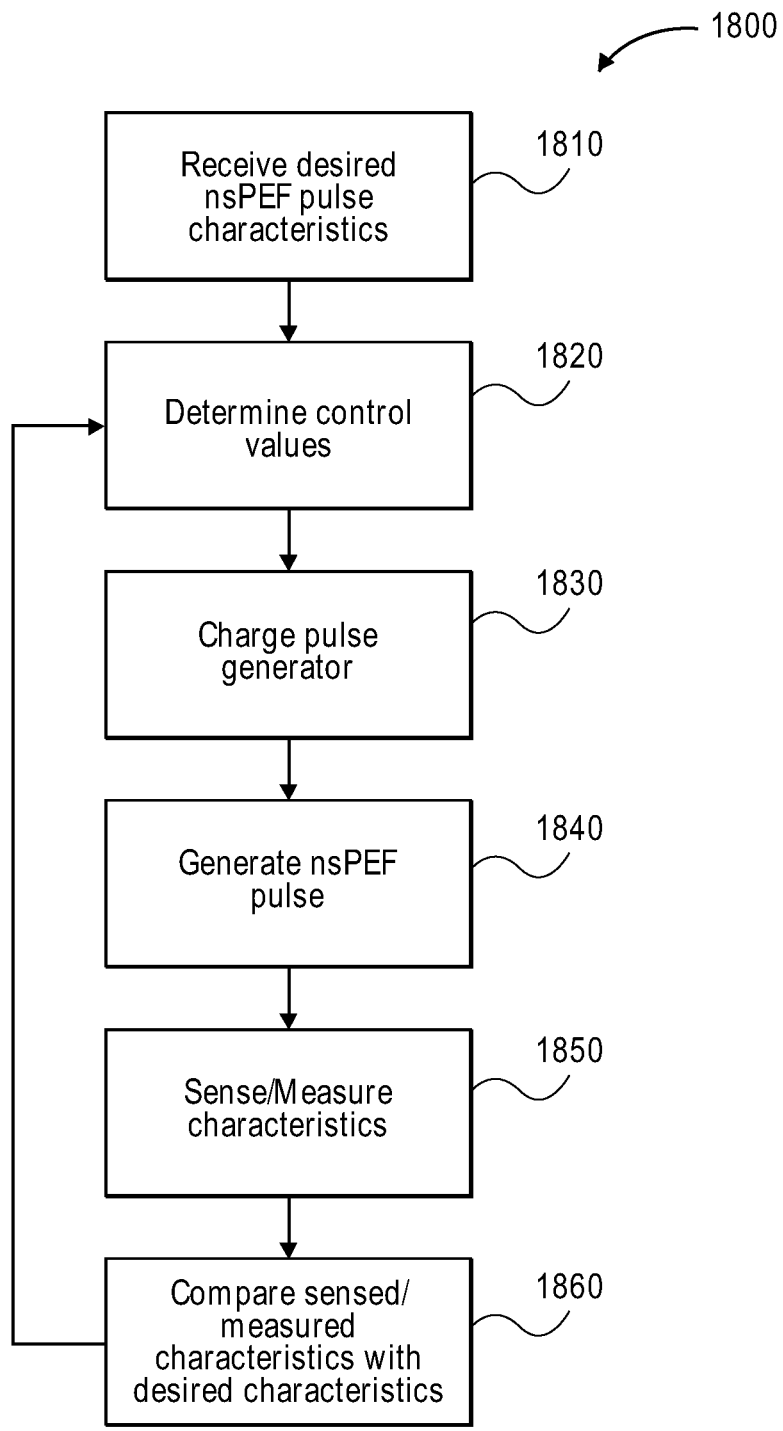
FIG. 18 is a flowchart illustration of methods of using an nsPEF treatment system.

FIG. 18 is a flowchart illustration of a method 1800 of using an nsPEF treatment system, such as nsPEF treatment system 1550 of FIG. 15. In the method, the nsPEF treatment system implements a feedback loop to control a parameter of the treatment. Because of one or more factors including, but not limited to, manufacturing variation, temperature, and system age, realized or measured parameters during treatment tend to have values somewhat different from the corresponding values with which the system was programmed. To increase accuracy of the system, the feedback loop actively measures and controls realized parameters so that the measured parameters more closely match the desired or programmed values.

At 1810, information representing one or more desired characteristics of a patient or of nsPEF pulses to be applied to the patient is received at an interface, such as interface 1570 of nsPEF treatment system 1550.

At 1820, a controller, such as controller 1575 of nsPEF treatment system 1550, generates control values corresponding with the values of the desired characteristics received at the interface.

At 1830, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller, where the received one or more control signals correspond with one or more control values generated at 1820.

At 1840, at least one nsPEF pulse is generated. In some embodiments, the at least one generated nsPEF pulse is applied to the patient. For example, in response to one or more control signals from the controller, the pulse generator may generate the nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 1850, one or more electrical characteristics of the nsPEF pulse or characteristics of the patient are measured or sensed, for example, while the nsPEF pulse is applied to the patient.

At 1860, a value of the measured or sensed characteristic is compared with the value of a corresponding desired characteristic as represented by the received information at 1810.

Returning to 1820, the controller modifies the control values corresponding with the values of the desired characteristics received at the interface according to the results of the comparison performed at 1860. The controller is configured to modify the control values so that, because of the modification to the control value, the value of a next measured or sensed characteristic is expected to be closer to the desired value of the characteristic than the value of the previously measured or sensed characteristic.

In some embodiments, the measured or sensed characteristic may include electrical characteristics of the nsPEF pulse, such as amplitude, pulse width, frequency, current, pulse shape, power, and energy. In some embodiments, a statistical value of one or more of amplitude, pulse width, frequency, current, pulse shape, power, and energy, such as average, standard deviation, median, minimum, and maximum is additionally or alternatively used. In some embodiments, an instantaneous value of one or more of amplitude, pulse width, frequency, current, pulse shape, power, and energy, such as average, standard deviation, median, minimum, and maximum is additionally or alternatively used. Other measured or sensed characteristics may be used.

In some embodiments, the measured or sensed characteristic may additionally or alternatively include an effect of the nsPEF pulse, such as a temperature of the tissue of the patient, a conductivity of the tissue of the patient, and arcing at the nsPEF pulse delivery electrode.

In some embodiments, the measured or sensed characteristic may additionally or alternatively include an environmental characteristic, such as a temperature, a humidity, and a chemical concentration.

Figure 19:
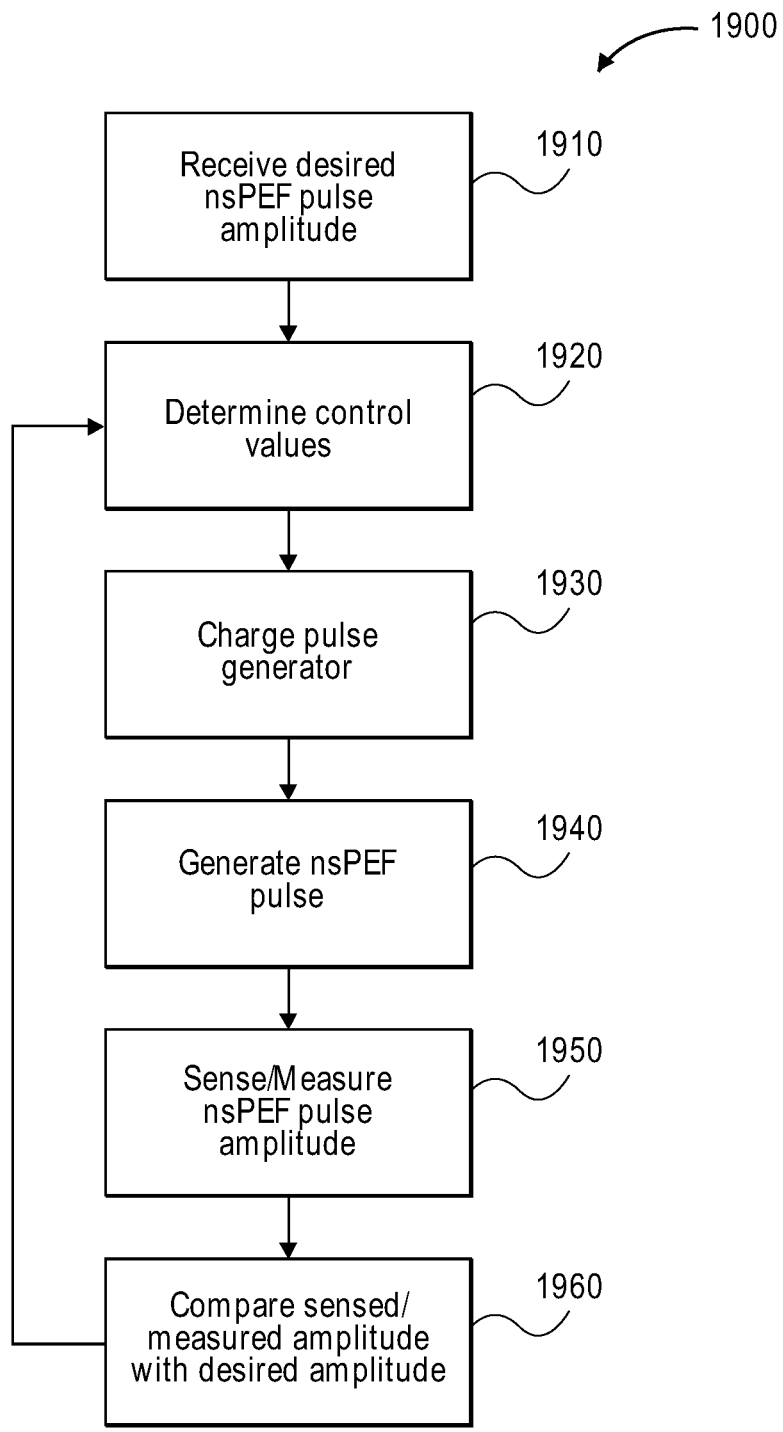
FIG. 19 is a flowchart illustration of methods of using an nsPEF treatment system.

FIG. 19 is a flowchart illustration of a method 1900 of using an nsPEF treatment system, such as nsPEF treatment system 1550 of FIG. 15.

At 1910, information representing a current or voltage amplitude of nsPEF pulses to be applied to the patient is received at an interface, such as interface 1570 of nsPEF treatment system 1550.

At 1920, a controller, such as controller 1575 of nsPEF treatment system 1550, generates control values corresponding with the desired amplitude.

At 1930, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller, where the received one or more control signals correspond with one or more control values generated at 1920.

At 1940, at least one nsPEF pulse is generated. In some embodiments, the at least one generated nsPEF pulse is applied to the patient. For example, in response to one or more control signals from the controller, the pulse generator may generate an nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 1950, the amplitude of the nsPEF pulse is measured or sensed, for example, while the nsPEF pulse is applied to the patient.

At 1960, a value of the measured or sensed amplitude is compared with the amplitude as represented by the received information at 1910.

Returning to 1920, the controller modifies the control values corresponding with the values of the desired amplitude received at the interface according to the results of the comparison performed at 1960. The controller is configured to modify the control values so that if the measured or sensed value of the amplitude is less than the desired amplitude, the modified control values will cause the power supply to charge the pulse generator with a voltage of greater value than previously used. Likewise, the controller is additionally configured to modify the control values so that if the measured or sensed value of the amplitude is greater than the desired amplitude, the modified control values will cause the power supply to charge the pulse generator with a voltage of less value than previously used.

Figure 20:
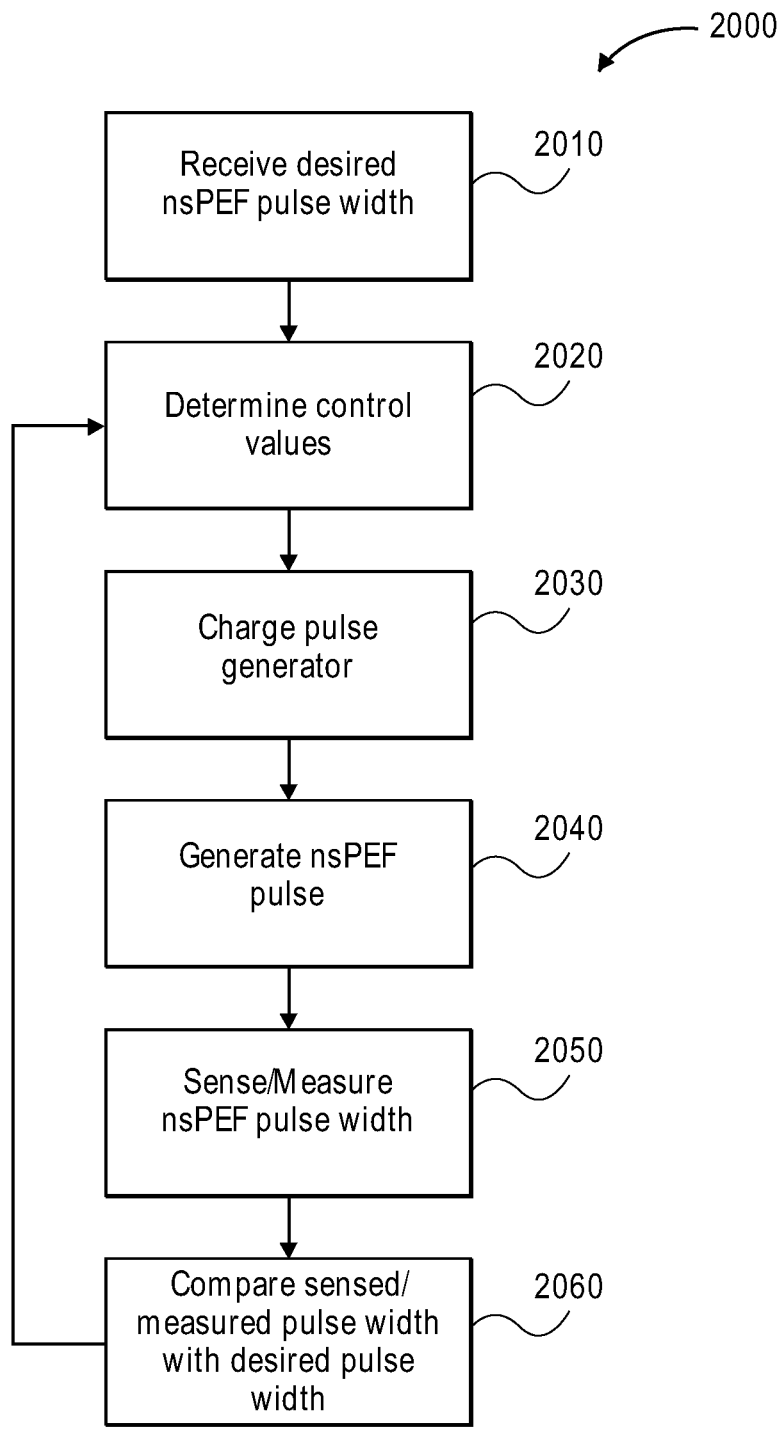
FIG. 20 is a flowchart illustration of methods of using an nsPEF treatment system.

FIG. 20 is a flowchart illustration of a method 2000 of using an nsPEF treatment system, such as nsPEF treatment system 1550 of FIG. 15.

At 2010, information representing a pulse width of nsPEF pulses to be applied to the patient is received at an interface, such as interface 1570 of nsPEF treatment system 1550.

At 2020, a controller, such as controller 1575 of nsPEF treatment system 1550, generates control values corresponding with the desired pulse width.

At 2030, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2040, at least one nsPEF pulse is generated. In some embodiments, the at least one generated nsPEF pulse is applied to the patient. For example, in response to one or more control signals from the controller, the pulse generator may generate an nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 2050, the pulse width of the nsPEF pulse is measured or sensed, for example, while the nsPEF pulse is applied to the patient.

At 2060, a value of the measured or sensed pulse width is compared with the pulse width as represented by the received information at 2010.

Returning to 2020, the controller modifies the control values corresponding with the values of the desired pulse width received at the interface according to the results of the comparison performed at 2060. The controller is configured to modify the control values so that if the measured or sensed value of the pulse width is less than the desired pulse width, the modified control values will cause the pulse generator to generate further nsPEF pulses with a pulse width of greater value than previously generated. Likewise, the controller is configured to modify the control values so that if the measured or sensed value of the pulse width is greater than the desired pulse width, the modified control values will cause the pulse generator to generate further nsPEF pulses having a pulse width of less value than previously generated.

Figure 21:
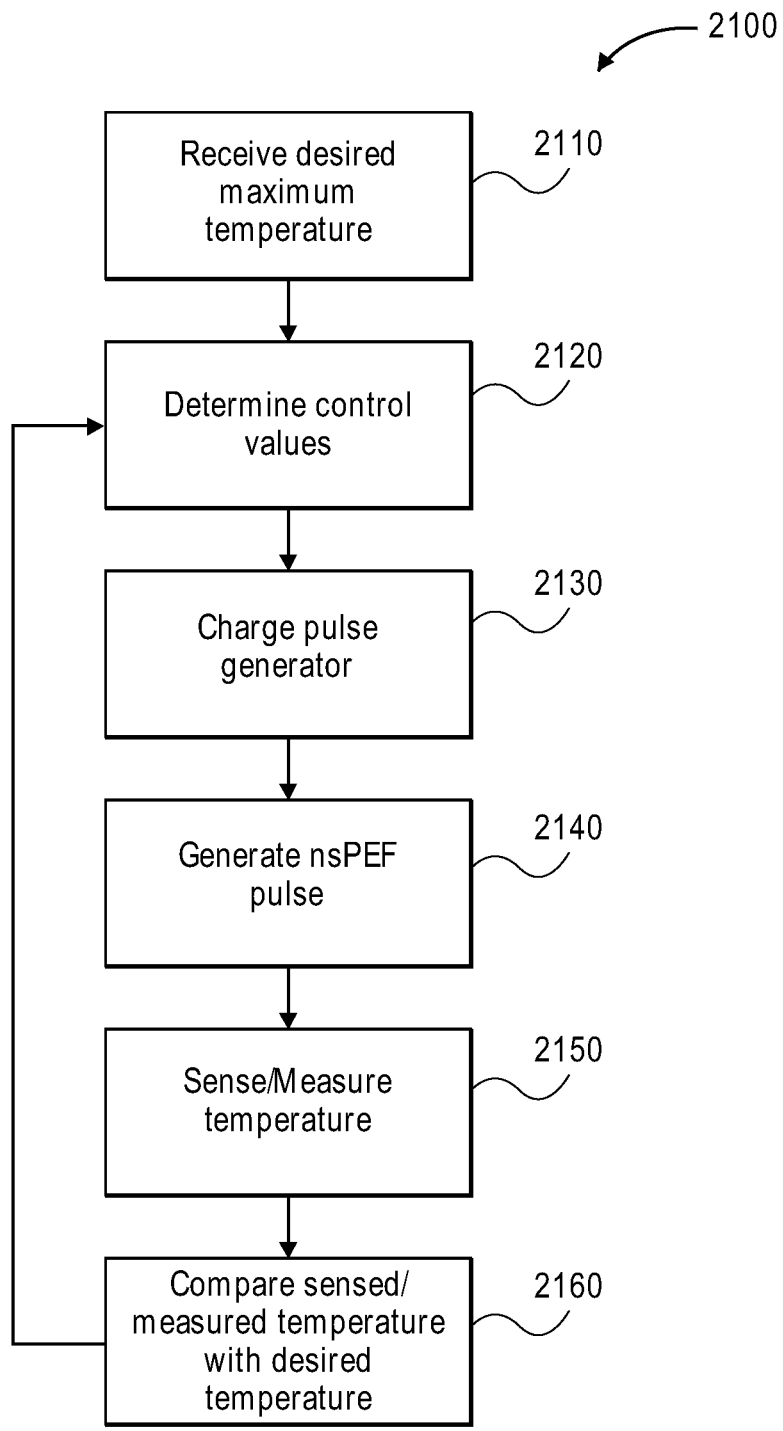
FIG. 21 is a flowchart illustration of methods of using an nsPEF treatment system.

FIG. 21 is a flowchart illustration of a method 2100 of using an nsPEF treatment system, such as nsPEF treatment system 1550 of FIG. 15.

At 2110, information representing a maximum tissue temperature of the patient being treated with nsPEF pulses is received at an interface, such as interface 1570 of nsPEF treatment system 1550.

At 2120, a controller, such as controller 1575 of nsPEF treatment system 1550, generates control values corresponding with the desired maximum tissue temperature.

At 2130, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2140, one or more nsPEF pulses are generated. In some embodiments, the generated nsPEF pulses are applied to the patient. For example, in response to one or more control signals from the controller, the pulse generator may generate the nsPEF pulses. In addition, an electrode, such as electrode 1565, may apply the nsPEF pulses to the patient. In some embodiments, the nsPEF pulses are applied to the patient as part of a treatment regimen. In some embodiments, the nsPEF pulses are applied to the patient as part of a characterization, set up, or calibration of the nsPEF treatment system. In some embodiments, the nsPEF pulses are not applied to the patient.

At 2150, the temperature of the patient is measured or sensed with a temperature sensor, for example, while the nsPEF pulses are applied to the patient.

At 2160, a value of the measured or sensed temperature is compared with the maximum temperature as represented by the received information at 2110.

Returning to 2120, the controller modifies the control values corresponding with the values of the desired maximum temperature received at the interface according to the results of the comparison performed at 2160. The controller is configured to modify the control values so that if the measured or sensed value of the temperature is greater than the maximum temperature or is greater than a threshold less than the maximum temperature, the modified control values will cause the nsPEF treatment system to deliver less power to the patient. For example, the modified control values may cause nsPEF pulses having less pulse width to be generated. Alternatively or additionally, the modified control values may cause nsPEF pulses with lower frequency to be generated. Alternatively or additionally, the modified control values may cause nsPEF pulses with lower voltage to be generated.

Figure 22:
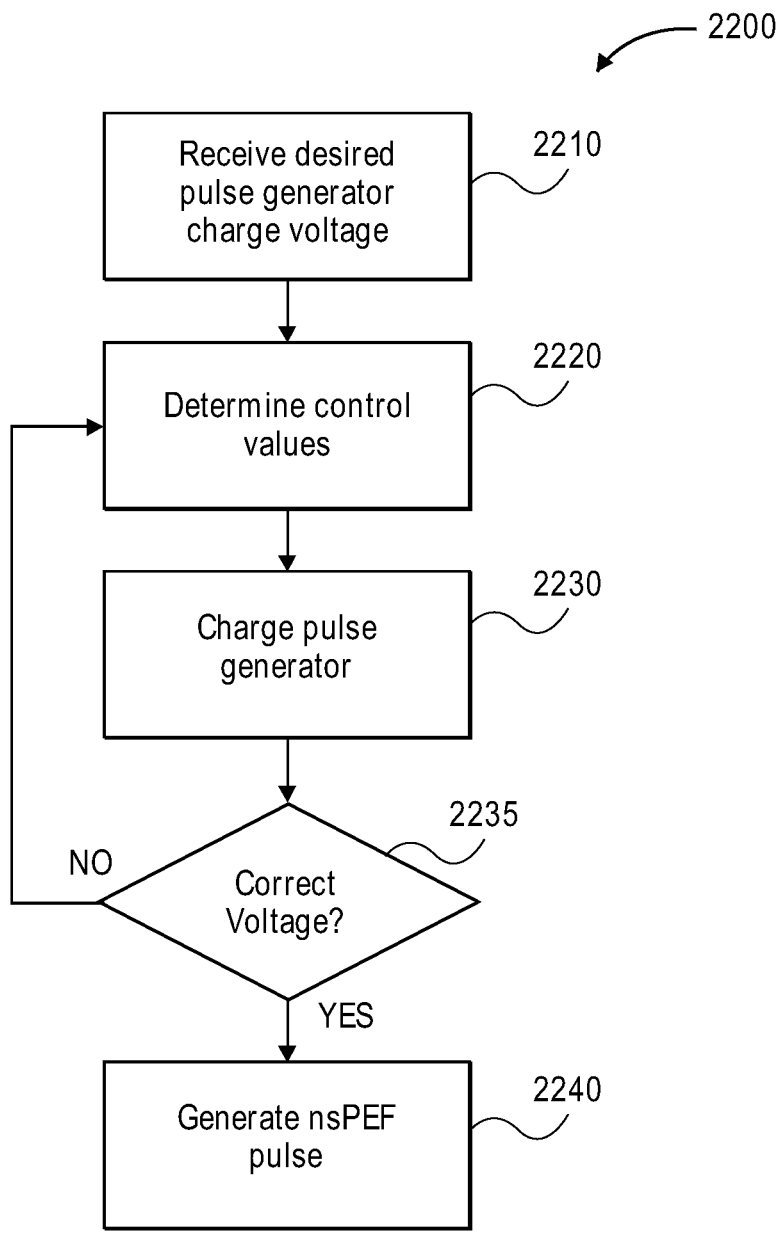
FIG. 22 is a flowchart illustration of a method of using an nsPEF treatment system.

FIG. 22 is a flowchart illustration of a method 2200 of using an nsPEF treatment system, such as nsPEF treatment system 1550 of FIG. 15.

At 2210, information representing a desired pulse generator charge voltage is received, for example, at an interface, such as interface 1570 of nsPEF treatment system 1550. In some embodiments, the desired pulse generator charge voltage is received at a controller, such as controller 1575 of nsPEF treatment system 1550.

At 2220, a controller, such as controller 1575 of nsPEF treatment system 1550, generates control values corresponding with the desired pulse generator charge voltage.

At 2230, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2235, the charge of the pulse generator is sensed and compared with the desired pulse generator charge voltage. For example, the controller may sense the voltage of the charged pulse generator and compare the sensed voltage with the desired pulse generator charge voltage.

If the difference between the sensed voltage and the desired pulse generator voltage falls outside an acceptable limit window, the method returns to 2220, where the controller generates new control values based on the desired pulse generator charge voltage and on the sensed voltage.

If the difference between the sensed voltage and the desired pulse generator voltage falls within an acceptable window, at 2140, one or more nsPEF pulses are generated. In some embodiments, the generated nsPEF pulses are applied to the patient. For example, in response to one or more control signals from the controller, the pulse generator may generate the nsPEF pulses. In addition, an electrode, such as electrode 1565, may apply the nsPEF pulses to the patient. In some embodiments, the nsPEF pulses are applied to the patient as part of a treatment regimen. In some embodiments, the nsPEF pulses are applied to the patient as part of a characterization, set up, or calibration of the nsPEF treatment system. In some embodiments, the nsPEF pulses are not applied to the patient.

Figure 23:
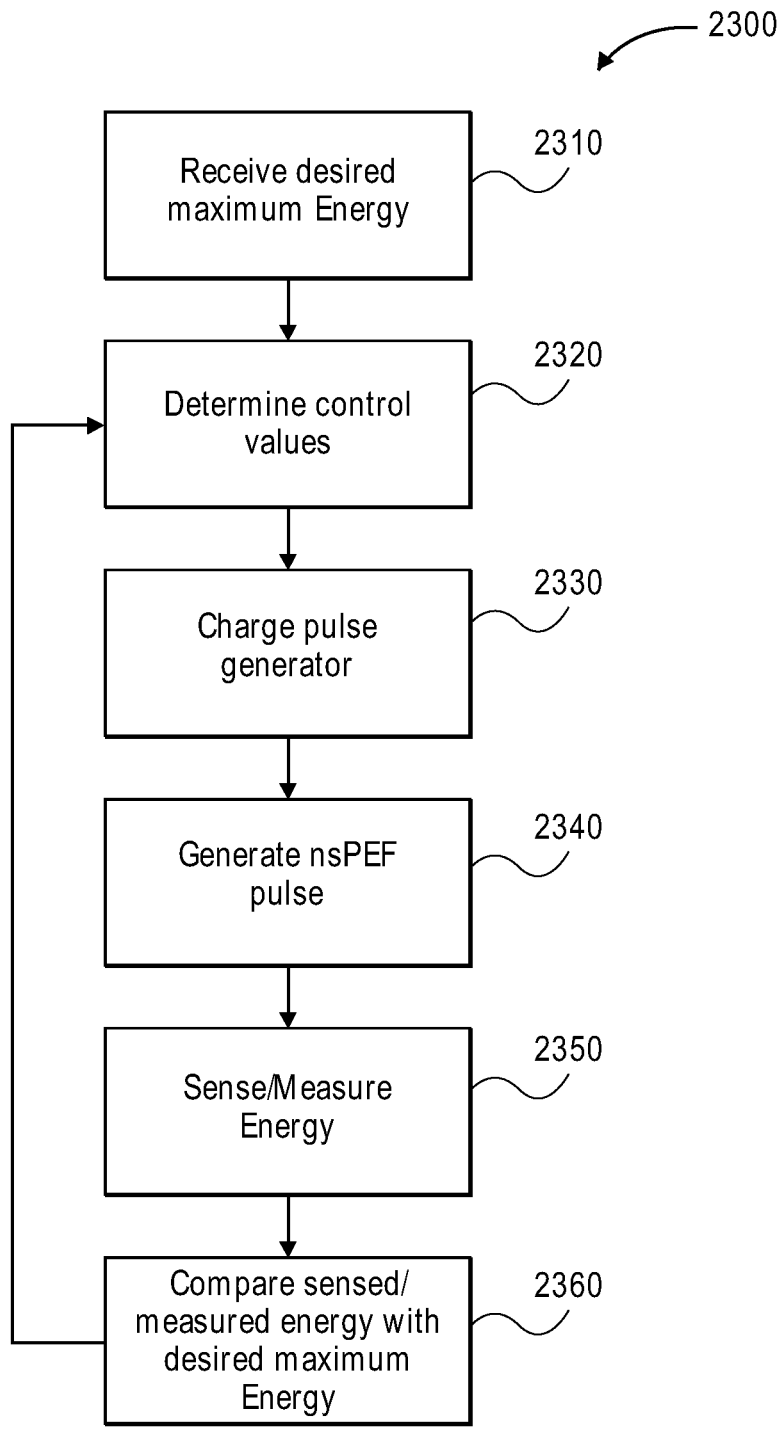
FIG. 23 is a flowchart illustration of a method of using an nsPEF treatment system.

FIG. 22 is a flowchart illustration of a method 2200 of using an nsPEF treatment system, such as nsPEF treatment system 1550 of FIG. 15. FIG. 23 is a flowchart illustration of a method 2300 of using an nsPEF treatment system, such as nsPEF treatment system 1550 of FIG. 15.

At 2310, information representing at least one of a maximum energy and a maximum average power to be delivered to the patient being treated with nsPEF pulses is received at an interface, such as interface 1570 of nsPEF treatment system 1550.

At 2320, a controller, such as controller 1575 of nsPEF treatment system 1550, generates control values corresponding with at least one of the desired maximum energy, the desired maximum power, one or more desired characteristics of a patient, and one or more desired characteristics of nsPEF pulses to be applied to the patient.

At 2330, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2340, one or more nsPEF pulses are generated. In some embodiments, the generated nsPEF pulses are applied to the patient. For example, in response to one or more control signals from the controller, the pulse generator may generate the nsPEF pulses. In addition, an electrode, such as electrode 1565, may apply the nsPEF pulses to the patient. In some embodiments, the nsPEF pulses are applied to the patient as part of a treatment regimen. In some embodiments, the nsPEF pulses are applied to the patient as part of a characterization, set up, or calibration of the nsPEF treatment system. In some embodiments, the nsPEF pulses are not applied to the patient.

At 2350, the energy of the nsPEF pulses is determined, for example, by measuring and integrating the product of instantaneous current and voltage values of the nsPEF pulses applied to the patient. The measured or sensed energy may be added to previously determined energy values to determine a total energy applied to the patient. Alternatively or additionally, an average power for a time duration may be determined, for example, by dividing the total energy delivered during the duration by the time of the duration.

At 2360, the processor may compare the total energy applied to the patient and the received maximum energy. Additionally or alternatively, the processor may compare the average power applied to the patient and the received maximum average power.

Returning to 2320, the controller modifies the control values according to the results of the comparison performed at 2360. The controller is configured to modify the control values so that if the measured or sensed value of the energy or average power is greater than the maximum desired energy or desired average power, or is greater than a threshold less than the maximum desired energy or desired average power, the modified control values will cause the nsPEF treatment system to deliver less power to the patient. For example, the modified control values may cause nsPEF pulses having less pulse width to be generated. Alternatively or additionally, the modified control values may cause nsPEF pulses with lower frequency to be generated. Alternatively or additionally, the modified control values may cause nsPEF pulses with lower voltage to be generated.

Figure 24:
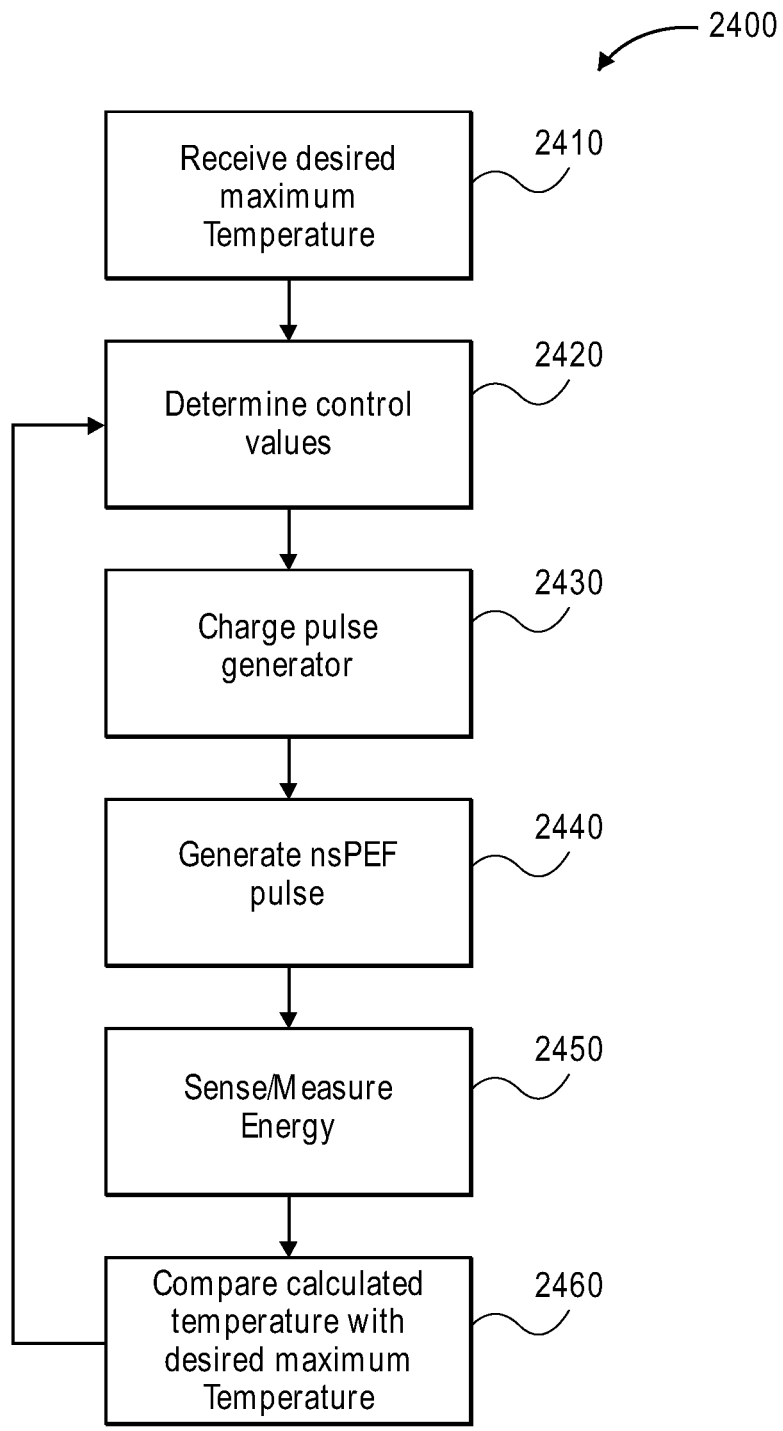
FIG. 24 is a flowchart illustration of a method of using an nsPEF treatment system.

FIG. 24 is a flowchart illustration of a method 2400 of using an nsPEF treatment system, such as nsPEF treatment system 1550 of FIG. 15.

At 2410, information representing a maximum tissue temperature of the patient being treated with nsPEF pulses is received at an interface, such as interface 1570 of nsPEF treatment system 1550.

At 2420, a controller, such as controller 1575 of nsPEF treatment system 1550, generates control values corresponding with the desired maximum tissue temperature.

At 2430, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller.

At 2440, one or more nsPEF pulses are generated. In some embodiments, the generated nsPEF pulses are applied to the patient. For example, in response to one or more control signals from the controller, the pulse generator may generate the nsPEF pulses. In addition, an electrode, such as electrode 1565, may apply the nsPEF pulses to the patient. In some embodiments, the nsPEF pulses are applied to the patient as part of a treatment regimen. In some embodiments, the nsPEF pulses are applied to the patient as part of a characterization, set up, or calibration of the nsPEF treatment system. In some embodiments, the nsPEF pulses are not applied to the patient.

At 2450, the energy of the nsPEF pulses is determined, for example, by measuring and integrating instantaneous current and voltage values of the nsPEF pulses applied to the patient. The measured or sensed energy may be added to previously determined energy values to determine a total energy applied to the patient. Alternatively or additionally, an average power for a time duration may be determined, for example, by dividing the total energy delivered during the duration by the time of the duration.

Based on one or more of the determined total energy and average power, a tissue temperature may be calculated. For example, temperature and thermal conductivity characteristics of the surrounding tissue and environment may be known and used to calculate a tissue temperature based on these parameters and the determined total energy and/or average power. Alternatively, a temperature measurement may be made, for example, using a thermocouple or a thermometer.

At 2460, the processor may compare the value of the calculated or measured temperature with the maximum temperature as represented by the received information at 2410.

Returning to 2420, the controller modifies the control values corresponding with the values of the desired maximum temperature received at the interface according to the results of the comparison performed at 2460. The controller is configured to modify the control values so that if the calculated or measured value of the temperature is greater than the maximum temperature or is greater than a threshold less than the maximum temperature, the modified control values will cause the nsPEF treatment system to deliver less power to the patient. For example, the modified control values may cause nsPEF pulses having less pulse width to be generated. Alternatively or additionally, the modified control values may cause nsPEF pulses with lower frequency to be generated. Alternatively or additionally, the modified control values may cause nsPEF pulses with lower voltage to be generated. In some embodiments of method 2400, tissue temperature corresponding with the calculated tissue temperature is not determined using a thermal sensor.

Figure 25:
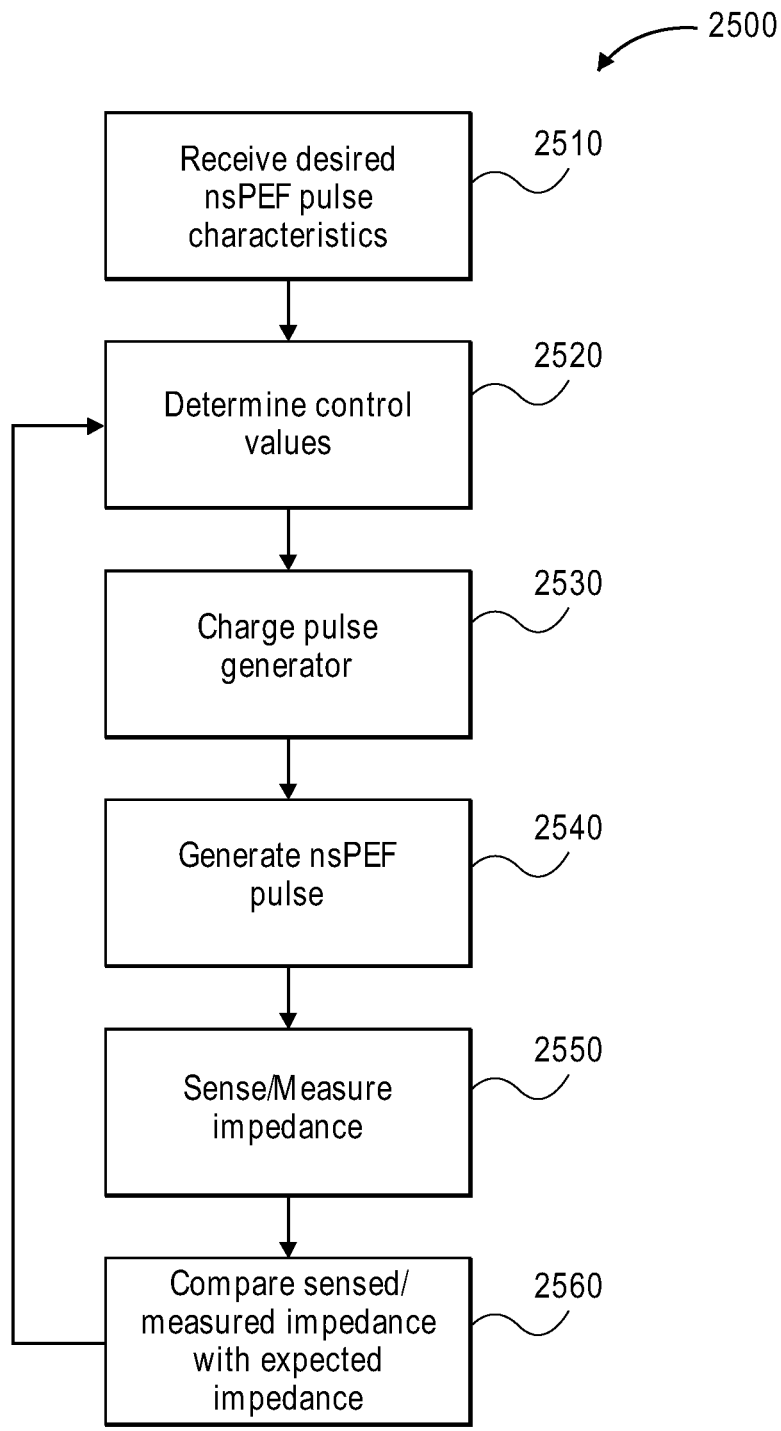
FIG. 25 is a flowchart illustration of a method of using an nsPEF treatment system.

FIG. 25 is a flowchart illustration of a method 2500 of using an nsPEF treatment system, such as nsPEF treatment system 1550 of FIG. 15.

At 2510, information representing one or more desired characteristics of a patient or of nsPEF pulses to be applied to the patient is received at an interface, such as interface 1570 of nsPEF treatment system 1550.

At 2520, a controller, such as controller 1575 of nsPEF treatment system 1550, generates control values corresponding with the values of the desired characteristics received at the interface.

At 2530, a power supply, such as power supply 1560 of nsPEF treatment system 1550, charges a pulse generator, such as pulse generator 1555 of nsPEF treatment system 1550. The power supply charges the pulse generator with a voltage value determined based on one or more control signals received from the controller, where the received one or more control signals correspond with one or more control values generated at 2520.

At 2540, at least one nsPEF pulse is generated. In some embodiments, the at least one generated nsPEF pulse is applied to the patient. For example, in response to one or more control signals from the controller, the pulse generator may generate the nsPEF pulse. In addition, an electrode, such as electrode 1565, may apply the nsPEF pulse to the patient. In some embodiments, the nsPEF pulse is applied to the patient as part of a treatment regimen. In some embodiments, the nsPEF pulse is applied to the patient as part of a characterization, set up, or calibration of the nsPEF treatment system. In some embodiments, the nsPEF pulse is not applied to the patient.

At 2550, one or more electrical characteristics of the nsPEF pulse or of the patient are measured or sensed, for example, while the nsPEF pulse is applied to the patient to determine a load impedance. For example, the nsPEF pulse voltage and current may be measured to determine the load impedance.

At 2560, a value of the measured or sensed load impedance is compared with the value of a corresponding expected load impedance.

Returning to 2520, the controller conditionally modifies the control values corresponding with the values of the desired characteristics received at the interface according to the results of the comparison performed at 2560. The controller is configured to modify control values so that, for example, if the measured impedance is greater than a threshold, the control values are modified such that the nsPEF treatment system stops generating nsPEF pulses. The high measured impedance may be an indication that the nsPEF treatment system should not continue generating nsPEF pulses because, for example, the nsPEF pulse delivery electrodes are no longer connected to the patient.

In some embodiments, the controller is configured to modify control values so that, for example, if the measured impedance is outside an expected range, the control values are set such that the nsPEF treatment system generates low voltage nsPEF pulses. The measured impedance being outside the expected range may be an indication that the nsPEF pulse delivery electrodes are not properly connected to the patient. The low voltage nsPEF pulses may be used until the measured load impedance is within the expected range.

In some embodiments, the nsPEF treatment system is configured to simultaneously perform more than one of the methods described above or other methods. For example, the nsPEF treatment system may be configured to modify one or more control values to realize multiple measured characteristics in the generated nsPEF pulses. For example, during a treatment session, the nsPEF treatment system may be configured to simultaneously measure and modify control parameters such that both the pulse width and the amplitude of the nsPEF pulses are actively controlled through feedback. In some embodiments, to ensure proper electrode connection, load impedance is measured based on one or more nsPEF pulses applied to the patient being treated, while the characteristics of the nsPEF pulses are actively controlled through feedback. In some embodiments, the pulse generator is charged using a feedback method having characteristics of method 2200 and the control values determining nsPEF characteristics are calculated based on measurements of one or more other methods.

Applying nsPEF to a tumor sufficient to stimulate apoptosis includes at least the electrical characteristics found experimentally. For example, a 100 ns long pulse with a 20 ns rise time to 30 kV/cm (kilovolts per centimeter) at 1 to 7 pulses per second (pps) for 500 to 2000 pulses has been found to be sufficient to stimulate apoptosis, depending on the tumor type. Pulsed electric fields of at least 20 kV/cm have been shown to be effective. A number of pulses greater than 50 pulses has also been shown to be effective. Current values between 12 A and 60 A resulted, depending on the electrode type and skin resistance.

The embodiments of pulse generators described herein have many uses. Cancer that has metastasized through a subject's bloodstream may be treated using nsPEF's immune stimulation properties. For treatment, circulating tumor cells (CTCs) are isolated from the bloodstream and amassed in vial, test tube, or other suitable in vitro environment. In some cases, there may only be a few (e.g., 5, 10), tumor cells that are collected and amassed. Through this mass, an nsPEF electric field is applied in order to treat the cells. This may cause calreticulin or one or more other damage-associated molecular patterns (DAMPs) to be expressed on the surface membranes of the tumor cells. The tumor cells may then be introduced back into the subject's bloodstream by injection, infusion, or otherwise.

In an alternative embodiment, single CTCs may also be isolated from the bloodstream, and each tumor cell treated individually. An automated system that captures CTCs in whole blood using iron nanoparticles coated with a polymer layer carrying biotin analogues and conjugated with antibodies for capturing CTCs can automatically capture the tumor cells, and a magnet and or centrifuge can separate them. After separation from the antibodies, the CTCs may be treated with nsPEF through a small capillary and then reintroduced to the patient's bloodstream.

While examples in the application discuss human and murine subjects, the treatment of other animals is contemplated. Agricultural animals, such as horses and cows, or racing animals, such as horses, may be treated. Companion animals, such as cats and dogs, may find special use with the treatments described herein. It may be difficult for a veterinarian to remove many tumors from a small animal, and cancers may be caught relatively late because the animals cannot communicate their advancing pain. Further, the risk inherent in reinjecting tumor cells—albeit treated tumor cells—may be worth the potential benefits of potentially halting a metastasized cancer in a loved pet.

The methods of the present invention can be used for the treatment of any type of cancer, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors, gastrointestinal carcinoid tumors, colon cancer, rectal cancer, anal cancer, bile duct cancer, small intestine cancer, and esophageal cancer; breast cancer; lung cancer; gallbladder cancer; liver cancer; pancreatic cancer; appendix cancer; prostate cancer; ovarian cancer; renal cancer (e.g., renal cell carcinoma); cancer of the central nervous system; skin cancer (e.g., melanoma); lymphomas; gliomas; choriocarcinomas; head and neck cancers; osteogenic sarcomas; and blood cancers.

Electrical characteristics of nsPEF treatments can be adjusted based on a size and/or a type of a tumor. Types of tumors may include tumors of different regions of the body, such as the cancerous tumors described above.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

As noted previously, all measurements, dimensions, and materials provided herein within the specification or within the figures are by way of example only.

A recitation of "a," "an," or "the" is intended to mean "one or more" unless specifically indicated to the contrary. Reference to a "first" component does not necessarily require that a second component be provided. Moreover reference to a "first" or a "second" component does not limit the referenced component to a particular location unless expressly stated.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

What is claimed is:
1. A sub-microsecond pulsed electric field generator system, comprising:
a controller, configured to generate a power supply control signal and a pulse generator control signal;

a power supply, configured to receive the power supply control signal and generate one or more power voltages based in part on the received power supply control signal; and a pulse generator circuit configured to receive the one or more power voltages and the pulse generator control signal, and to generate one or more pulses based at least in part on the one or more power voltages received from the power supply and based at least in part on the pulse generator control signal received from the controller, wherein the pulse generator circuit comprises a plurality of pulse generator stages, and wherein at least one pulse generator stage of the plurality of pulse generator stages comprises:
 a switch stack including a plurality of switches connected in series;
 one or more switch drivers comprising a lossy transformer, the one or more switch drivers connecting to the plurality of switches and configured to generate switch control signal pulses for switching respective switches of the plurality of switches; and
 a capacitive element coupled to the switch stack.

2. The system of claim 1, wherein the at least one pulse generator stage further comprises a plurality of resistive elements coupled to the switch stack and the capacitive element, and wherein the at least one pulse generator stage is configured to be connected in parallel to at least one other of the plurality of pulse generator stages through the plurality of resistive elements and configured to charge the capacitive element to the one or more power voltages.

3. The system of claim 1, wherein the at least one pulse generator stage is configured to be connected in series to at least one other of the plurality of pulse generator stages through the switch stack in response to the switch control signal pulses from the one or more switch drivers closing the plurality of switches to generate the one or more pulses.

4. The system of claim 1, further comprising an interface configured to receive information indicating a desired value for a characteristic of or a result of the one or more pulses, wherein the controller is configured to generate at least one of the power supply control signal or the pulse generator control signal based at least partly on the desired value.

5. The system of claim 1, further comprising an electrode configured to apply the one or more pulses to a patient.

6. The system of claim 1, wherein the pulse generator circuit is a first pulse generator circuit of a plurality of pulse generator circuits connected in parallel.

7. The system of claim 6, wherein each pulse generator circuit further comprises a diode connected between an output of the respective pulse generator circuit and an output of the other pulse generator circuits, each respective diode configured to decouple the respective pulse generator circuit from the other pulse generator circuits.

8. The system of claim 1, wherein the one or more switch drivers comprises a respective switch driver for each respective switch of the plurality of switches in the switch stack, and wherein the switch control signal pulse generated by each respective switch driver is referenced to a voltage specific to the respective switch being driven.

9. The system of claim 1, wherein each of the plurality of switches has a breakdown voltage, wherein the one or more power voltages is greater than the breakdown voltage of each respective switch, and wherein the at least one pulse generator stage is configured to charge the capacitive element to the one or more power voltages.

10. The system of claim 1, wherein each of the plurality of switches is a power metal-oxide-semiconductor field-effect transistor (MOSFET).

11. The system of claim 1, wherein the pulse generator circuit comprises a driving circuit configured to generate a trigger pulse in response to the pulse generator control signal.

12. The system of claim 11, wherein the trigger pulse closes the plurality of switches substantially simultaneously.

13. A method of generating sub-microsecond pulsed electric field pulses, the method comprising:
 generating a power supply control signal with a controller;
 generating a pulse generator control signal with the controller;
 receiving the power supply control signal at a power supply;
 generating, with the power supply, one or more power voltages based in part on the power supply control signal;
 receiving the one or more power voltages and the pulse generator control signal at a pulse generator; and
 generating, with the pulse generator, one or more pulses based in part on the one or more power voltages received from the power supply and based in part on the pulse generator control signal received from the controller;
 wherein the pulse generator is a sub-microsecond pulse generator comprising a plurality of pulse generator stages and at least one pulse generator stage of the plurality of pulse generator stages comprises:
 a switch stack comprising a plurality of switches;
 a capacitive element coupled to the switch stack; and
 one or more switch drivers comprising a lossy transformer, the one or more switch drivers connecting to the plurality of switches and configured to generate switch control signal pulses for switching respective switches of the plurality of switches.

14. The method of claim 13, wherein generating the one or more pulses with the pulse generator comprises:
 charging the capacitive element in the at least one pulse generator stage to the one or more power voltages;
 generating, by a driving circuit, a trigger signal in response to receiving the pulse generator control signal; and
 activating, by the one or more switch drivers of the pulse generator, the switch stack to discharge the capacitive element in each of the at least one pulse generator stage in series to generate the one or more pulses.

15. The method of claim 13, further comprising applying the one or more pulses to a patient via an electrode.

16. The method of claim 13, further comprising:
 receiving information indicating a desired value for a characteristic of or a result of the one or more pulses via an interface; and
 generating at least one of the power supply control signal or the pulse generator control signal based at least partly on the desired value.

17. The method of claim 16, wherein the power supply, the controller, and the pulse generator collectively form a feedback loop which causes the characteristic of or the result of the one or more pulses to have a value substantially equal to the desired value.

18. The method of claim 17, wherein the feedback loop is controlled using at least one of:

a Proportional-Integral-Derivative (PID) method;
a lookup table to determine a next control signal value; and
a method including increasing or decreasing a next control signal value by a fixed amount.

19. The method of claim 13, further comprising generating one or more feedback signals with the pulse generator, an electrode, or both.

20. The method of claim 19, further comprising generating a signal representing a measured voltage with a voltage sensor, wherein the at least one of the one or more feedback signals represents the measured voltage.

21. The method of claim 19, further comprising generating a signal representing a measured current with a current sensor, wherein the at least one of the one or more feedback signals represents the measured current.

22. The method of claim 19, further comprising generating a signal representing a measured temperature with a temperature sensor in the electrode, wherein the at least one of the one or more feedback signals represents the measured temperature.

23. A nanosecond pulsed electric field (nsPEF) generator, comprising:
   a pulse generator circuit, comprising a plurality of stages, each stage comprising:
      first and second stage input terminals;
      first and second stage output terminals;
      a switch stack comprising a plurality of switches connected in series and coupled between the first stage input terminal and the second stage output terminal;
      one or more switch drivers connected to the plurality of switches;
      a capacitive element having first and second terminals, wherein the first terminal of the capacitive element is coupled to the second stage output terminal and the second terminal of the capacitive element is coupled to the first stage output terminal;
      a first resistive element coupled between the first stage input terminal and the first stage output terminal; and
      a second resistive element coupled between the second stage input terminal and the second stage output terminal;
   wherein the plurality of stages are coupled between input terminals and output terminals of the pulse generator circuit;
   a driving circuit coupled to the pulse generator circuit;
   a power supply coupled to the pulse generator circuit; and
   a controller coupled to the driving circuit;
   wherein, absent control signal pulses from the one or more switch drivers, the plurality of switches in each of the plurality of stages are open, charging the respective capacitive elements, in parallel, to a voltage of the power supply, and
   wherein the one or more switch drivers are configured to generate the control signal pulses for switching respective switches of the plurality of switches in response to a trigger pulse generated by the driving circuit in response to the controller sending a pulse generator control signal to the driving circuit, discharging the capacitive elements in series to generate one or more pulses across first and second power output terminals of the pulse generator circuit.

24. The nsPEF generator of claim 23, further comprising an electrode configured to apply the one or more pulses to a patient.

25. The nsPEF generator of claim 24, wherein the one or more switch drivers comprises a lossy transformer.

* * * * *